(12) United States Patent
Behnke et al.

(10) Patent No.: US 8,022,069 B2
(45) Date of Patent: Sep. 20, 2011

(54) SUBSTITUTED PIPERIDINES AS RENIN INHIBITORS

(75) Inventors: Dirk Behnke, Basel (CH); Peter Herold, Münchenstein (CH); Stjepan Jelakovic, Freiburg (DE); Robert Mah, Basel (CH); Vincenzo Tschinke, Binningen (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/865,932

(22) PCT Filed: Feb. 6, 2009

(86) PCT No.: PCT/EP2009/051350
§ 371 (c)(1),
(2), (4) Date: Aug. 16, 2010

(87) PCT Pub. No.: WO2009/098276
PCT Pub. Date: Aug. 13, 2009

(65) Prior Publication Data
US 2010/0331322 A1 Dec. 30, 2010

(30) Foreign Application Priority Data
Feb. 8, 2008 (EP) .................... 08101428

(51) Int. Cl.
*C07D 413/12* (2006.01)
*C07D 413/14* (2006.01)
*A61K 31/445* (2006.01)

(52) U.S. Cl. .................... 514/230.5; 544/105

(58) Field of Classification Search ............ 544/105; 514/230.5
See application file for complete search history.

(56) References Cited

FOREIGN PATENT DOCUMENTS

| WO | 2006/005741 A | 1/2006 |
|----|---------------|--------|
| WO | 2006/103275 A | 10/2006 |
| WO | 2006/103277 A | 10/2006 |

OTHER PUBLICATIONS

Chalmers (TiPS vol. 17, pp. 166-172 Apr. 1996).*
Yokokawa F et al: "Recent advances in the discovery of non-peptidic direct renin inhibitors as antihypertensives: New patent applications in years 2000-2008" Expert Opinion on Therapeutic Patents 200806 GB, vol. 18, No. 6, Jun. 2008, pp. 581-602, XP002505950.

* cited by examiner

*Primary Examiner* — Kahsay T Habte
(74) *Attorney, Agent, or Firm* — Wenderoth, Lind & Ponack, L.L.P.

(57) ABSTRACT

The present invention relates to compounds of the general formula (I) and the salts thereof, preferably the pharmaceutically acceptable salts thereof; in which R has the meaning explained in the description, a process for their preparation and the use of these compounds as medicines, especially as renin inhibitors.

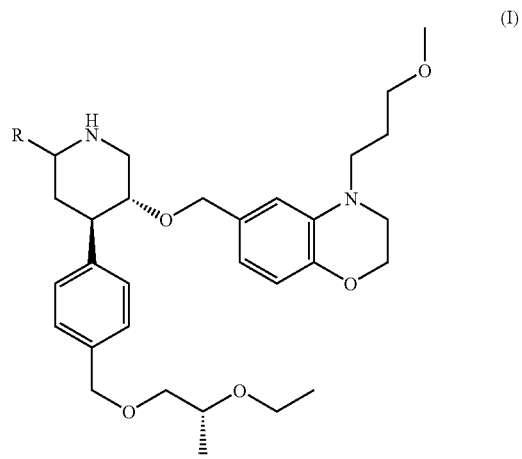

12 Claims, No Drawings

SUBSTITUTED PIPERIDINES AS RENIN INHIBITORS

This application is a U.S. national Phase filing of International Serial No. PCT/EP2009/051350 filed Feb, 6, 2009 and claims priority to EP application Serial No. 08101428.4 filed Feb. 8, 2008, the contents of which are incorporated herein by reference in their entirety.

FIELD OF THE INVENTION

The present invention relates to novel substituted 4-phenyl piperidines, to processes for their preparation and to the use of the compounds as medicines, in particular as renin inhibitors.

BACKGROUND OF THE INVENTION

Piperidine derivatives for use as medicines are known, for example from WO97/09311. However, especially with regard to renin inhibition, there is still a need for highly potent active ingredients. In this context, the improvement of a compound's pharmacokinetic properties, resulting in better oral bioavailability, and/or it's overall safety profile are at the forefront. Properties directed towards better bioavailability are, for example, increased absorption, metabolic stability or solubility, or optimized lipophilicity. Properties directed towards a better safety profile are, for example, increased selectivity against drug metabolizing enzymes such as the cytochrome P450 enzymes.

DETAILED DESCRIPTION OF THE INVENTION

The invention therefore provides substituted 4-phenyl piperidines of the general formula

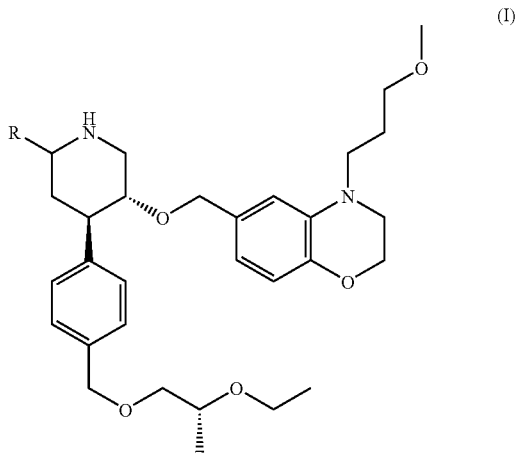

(I)

and their salts, preferably their pharmaceutically acceptable salts, in which
R is
$C_{2-8}$-alkenyl,
$C_{2-8}$-alkynyl,
$C_{0-8}$-alkyl-carbonyl-optionally N-mono-$C_{1-8}$-alkylated amino-$C_{1-8}$-alkyl,
$C_{3-8}$-cycloalkyl-$C_{0-8}$-alkyl,
$C_{1-8}$-alkyl-sulfonyl-$C_{1-8}$-alkyl,
optionally N-mono- or N,N-di-$C_{1-8}$-alkylated carbamoyl-$C_{0-8}$-alkyl,
optionally O—$C_{1-8}$-alkylated carboxyl-$C_{0-8}$-alkyl,
optionally N and/or N' mono-, di- or tri-$C_{1-8}$-alkylated ureido-$C_{1-8}$-alkyl,
heterocyclylcarbonyl-$C_{0-8}$-alkyl or
heterocyclyl-$C_{0-8}$-alkyl,
each of said radicals may be substituted, preferably by 1-4 substituents independently selected from
$C_{1-8}$-alkoxy,
$C_{1-8}$-alkoxy-$C_{1-8}$-alkoxy,
$C_{1-8}$-alkyl,
cyano,
halogen,
hydroxyl,
oxo,
trifluoromethoxy and
trifluoromethyl.

The meaning of "$C_0$-alkyl" in the above (and hereinafter) mentioned $C_{0-8}$-alkyl groups is a bond or, if located at a terminal position, a hydrogen atom.

Examples of $C_{1-8}$-alkyl radicals, which may be linear or branched, are methyl, ethyl, n-propyl, isopropyl, n-butyl, isobutyl, sec-butyl, tert-butyl, pentyl and hexyl respectively. Examples of $C_{1-8}$-alkoxy radicals, which may be linear or branched, are radicals such as methoxy, ethoxy, n-propoxy, isopropoxy, n-butoxy, isobutoxy, sec-butoxy and tert-butoxy. Examples of $C_{2-8}$-alkenyl radicals, which may be linear or branched, are, for example, vinyl and propenyl. Examples of $C_{2-8}$-alkynyl radicals, which may be linear or branched, are, for example, ethynyl. Examples of O—$C_{1-8}$-alkylated carboxyl are radicals such as methoxycarbonyl, ethoxycarbonyl, n-propoxycarbonyl, iso propoxycarbonyl, n-butoxycarbonyl, isobutoxycarbonyl, sec-butoxycarbonyl and tert-butoxycarbonyl. Examples of $C_{0-8}$-alkylcarbonylamino are for example formylamino, acetylamino, n-propionylamino, isopropionylamino, n-butylcarbonylamino, isobutylcarbonylamino, sec-butylcarbonylamino and tert-butylcarbonylamino. Examples of optionally N and/or N' mono-, -di- or -tri-$C_{1-8}$-alkylated ureido are radicals such as ureido, 1-methyl-ureido, 3-methyl-ureido, trimethyl-ureido, 1-ethyl-ureido, 3-ethyl-ureido, triethyl-ureido, 1-ethyl-3-methyl-ureido, 3-ethyl-1-methyl-ureido. Examples of optionally N-mono- or N,N-di-$C_{1-8}$-alkylated carbamoyl-$C_{0-8}$-alkyl are radicals such as carbamoyl, N-methyl carbamoyl, N-ethyl carbamoyl, N-propyl carbamoyl, N,N-di-methyl carbamoyl, N,N-di-ethyl carbamoyl, N,N-di-propyl carbamoyl, carbamoyl-methyl, N-methyl carbamoyl-methyl, N-ethyl carbamoyl-methyl, N-propyl carbamoyl-methyl, N,N-di-methyl carbamoyl-methyl, N,N-di-ethyl carbamoyl-methyl, N,N-di-propyl carbamoyl-methyl, carbamoyl-ethyl, N-methyl carbamoyl-ethyl, N-ethyl carbamoyl-ethyl, N-propyl carbamoyl-ethyl, N,N-di-methyl carbamoyl-ethyl, N,N-di-ethyl carbamoyl-ethyl, N,N-di-propyl carbamoyl-ethyl, carbamoyl-2-propyl, N-methyl carbamoyl-2-propyl, N-ethyl carbamoyl-2-propyl, N-propyl carbamoyl-2-propyl, N,N-di-methyl carbamoyl-2-propyl, N,N-di-ethyl carbamoyl-2-propyl, N,N-di-propyl carbamoyl-2-propyl, carbamoyl-(2-methyl-2-butyl), N-methyl carbamoyl-(2-methyl-2-butyl), N-ethyl carbamoyl-(2-methyl-2-butyl), N-propyl carbamoyl-(2-methyl-2-butyl), N,N-di-methyl carbamoyl-(2-methyl-2-butyl), N,N-di-ethyl carbamoyl-(2-methyl-2-butyl), N,N-di-propyl carbamoyl-(2-methyl-2-butyl).

The term heterocyclyl refers to 3-8 membered monocyclic, saturated or unsaturated heterocyclic radicals having 1 to 4 nitrogen and/or 1 or 2 sulfur or oxygen atoms, for example saturated or unsaturated N-containing $C_{3-8}$-heterocyclyl. The heterocyclyl radicals may be substituted one or more times, such as, for example, substituted once or twice by $C_{1-8}$-alkoxy, $C_{1-8}$-alkyl, cyano, halogen, hydroxy, trifluoromethoxy or trifluoromethyl. Heterocyclyl radicals which comprise a nitrogen atom may be linked either via the N atom or via a C atom to the remainder of the molecule. Examples of such heterocyclyl radicals are imidazolyl, morpholinyl, oxetanyl, oxiranyl, pyrazolyl, pyridyl, pyrrolidinyl, tetrahydrofuranyl, tetrahydropyranyl, tetrazolyl, thiazolyl and triazolyl. Examples of preferred heterocyclic radicals are morpholinyl, tetrazolyl and triazolyl.

Halogen is fluoro, chloro, bromo or iodo.

Cycloalkyl refers to a saturated cyclic hydrocarbon radicals having 3 to 8 carbon atoms, for example cyclopropyl, cyclobutyl or cyclopentyl and may be unsubstituted or substituted once or twice by $C_{1-8}$-alkoxy, $C_{1-8}$-alkoxy-$C_{1-8}$-alkyl, optionally halogen substituted $C_{1-8}$-alkyl or halogen.

Salts are primarily the pharmaceutically usable or nontoxic salts of compounds of formula (I). The term "pharmaceutically useable salts" encompasses salts with inorganic or organic acids, such as hydrochloric acid, hydrobromic acid, nitric acid, sulfuric acid, phosphoric acid, citric acid, formic acid, maleic acid, acetic acid, succinic acid, tartaric acid, methanesulfonic acid, p-toluenesulfonic acid and the like.

Salts of compounds having salt-forming groups are in particular acid addition salts, salts with bases, or, in the presence of a plurality of salt-forming groups, in some cases also mixed salts or internal salts.

Such salts are formed, for example, from compounds of formula (I) with an acidic group, for example a carboxyl or sulfonyl group, and are, for example, the salts thereof with suitable bases such as non-toxic metal salts derived from metals of group Ia, Ib, IIa and IIb of the Periodic Table of the Elements, for example alkali metal, in particular lithium, sodium, or potassium, salts, alkaline earth metal salts, for example magnesium or calcium salts, and also zinc salts and ammonium salts, including those salts which are formed with organic amines, such as optionally hydroxy-substituted mono-, di- or trialkylamines, in particular mono-, di- or tri (lower alkyl)amines, or with quaternary ammonium bases, e.g. methyl-, ethyl-, diethyl- or triethylamine, mono-, bis- or tris(2-hydroxy(lower alkyl))amines, such as ethanol-, diethanol- or triethanolamine, tris(hydroxymethyl)methylamine or 2-hydroxy-tert-butylamine, N,N-di(lower alkyl)-N-(hydroxy (lower alkyl))amine, such as N,N-di-N-dimethyl-N-(2-hydroxyethyl)amine, or N-methyl-D-glucamine, or quaternary ammonium hydroxides such as tetrabutyl ammoniumhydroxide. The compounds of formula (I) having a basic group, for example an amino group, may form acid addition salts, for example with suitable inorganic acids, e.g. hydrohalic acid such as hydrochloric acid, hydrobromic acid, sulfuric acid with replacement of one or both protons, phosphoric acid with replacement of one or more protons, e.g. orthophosphoric acid or metaphosphoric acid, or pyrophosphoric acid with replacement of one or more protons, or with organic carboxylic, sulfonic or phosphonic acids or N-substituted sulfamic acids, e.g. acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid, isonicotinic acid, and also amino acids, for example the alpha-amino acids mentioned above, and also methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, 2- or 3-phosphoglycerate, glucose 6-phosphate, N-cyclo-hexylsulfamic acid (with formation of the cyclamates) or with other acidic organic compounds such as ascorbic acid. Compounds of formula (I) having acidic and basic groups may also form internal salts.

Salts obtained may be converted to other salts in a manner known per se, acid addition salts, for example, by treating with a suitable metal salt such as a sodium, barium or silver salt, of another acid in a suitable solvent in which an inorganic salt which forms is insoluble and thus separates out of the reaction equilibrium, and base salts by release of the free acid and salt reformation.

The compounds of formula (I), including their salts, may also be obtained in the form of hydrates or include the solvent used for the crystallization.

For the isolation and purification, pharmaceutically unsuitable salts may also find use.

The compounds of formula (I) also include those compounds in which one or more atoms are replaced by their stable, non-radioactive isotopes; for example a hydrogen atom by deuterium.

The compounds of the formula (I) also include compounds that have been nitrosated through one or more sites such as oxygen (hydroxyl condensation), sulfur (sulfydryl condensation) and/or nitrogen. The nitrosated compounds of the present invention can be prepared using conventional methods known to one skilled in the art. For example, known methods for nitrosating compounds are described in WO2004/098538 A2.

The compounds of the formula (I) also include compounds that have been converted at one or more sites such that a nitrate-ester-containing linker is attached to an existing oxygen and/or nitrogen. Such "nitroderivatives" of the compounds of the present invention can be prepared using conventional methods known to one skilled in the art. For example, known methods for converting compounds into their nitroderivatives are described in WO2007/045551 A2.

The compounds of formula (I) have at least four asymmetric carbon atoms and may therefore be in the form of optically pure diastereomers, diastereomeric mixtures, diastereomeric racemates, mixtures of diastereomeric racemates or as meso compounds. The invention encompasses all of these forms. Diastereomeric mixtures, diastereomeric racemates or mixtures of diastereomeric racemates may be separated by customary procedures, for example by column chromatography, thin-layer chromatography, HPLC and the like.

The compounds of formula (I) may also be prepared in optically pure form. The separation into antipodes can be effected by procedures known per se, either preferably at an earlier synthetic stage by salt formation with an optically active acid, for example (+)- or (−)-mandelic acid and separation of the diastereomeric salts by fractional crystallization, or preferably at a relatively late stage by derivatizing with a chiral auxiliary building block, for example (+)- or (−)-camphanoyl chloride, and separation of the diastereomeric products by chromatography and/or crystallization and subsequent cleavage of the bonds to give the chiral auxiliary. The pure diastereomeric salts and derivatives may be analysed to determine the absolute configuration of the piperidine present with common spectroscopic procedures, and X-ray spectroscopy on single crystals constitutes a particularly suitable procedure.

It is possible for the configuration at individual chiral centres in a compound of formula (I) to be inverted selectively. For example, the configuration of asymmetric carbon atoms which bear nucleophilic substituents, such as amino or hydroxyl, may be inverted by second-order nucleophilic substitution, if appropriate after conversion of the bonded nucleophilic substituent to a suitable nucleofugic leaving group and reaction with a reagent which introduces the original substituents, or the configuration at carbon atoms having hydroxyl groups can be inverted by oxidation and reduction, analogously to the process in the European patent application EP-A-0 236 734. Also advantageous is the reactive functional modification of the hydroxyl group and subsequent replacement thereof by hydroxyl with inversion of configuration.

The compound groups mentioned below are not to be regarded as closed, but rather parts of these compound groups may be exchanged with one another or with the definitions given above or omitted in a sensible manner, for example to replace general by more specific definitions. The definitions are valid in accordance with general chemical principles, such as, for example, the common valences for atoms.

The compounds of formula e (I), (IA) and (IB) can be prepared in an analogous manner to preparation processes disclosed in the literature. Similar preparation processes are described for example in WO 97/09311 and in WO06/103275. Details of the specific preparation variants can be found in the examples.

Preferred compounds are those of the general formulae (IA) or (IB)

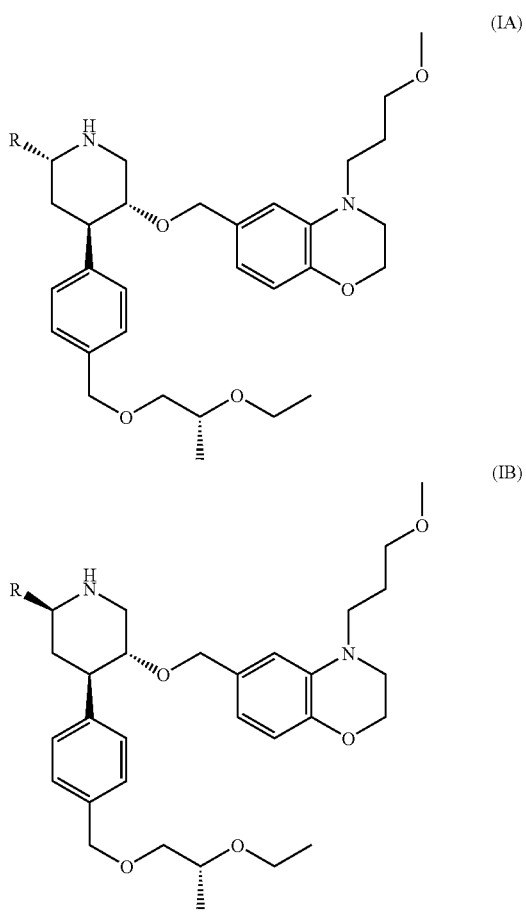

and the salts thereof, preferably the pharmaceutically acceptable salts thereof, are compounds in which R is as defined above for the compounds of the formula (I).

A further, preferred group of compounds of the formula (I), or more preferably of the formula (IA) or (IB), and the salts thereof, preferably the pharmaceutically acceptable salts thereof, are compounds in which R is
$C_{0-8}$-alkyl-carbonyl-optionally N-mono-$C_{1-8}$-alkylated amino-$C_{1-8}$-alkyl,
optionally substituted, preferably by 1-2 substituents independently selected from
$C_{1-8}$-alkoxy,
$C_{1-8}$-alkoxy-$C_{1-8}$-alkoxy,
$C_{1-8}$-alkyl,
cyano,
halogen,
hydroxyl,
oxo,
trifluoromethoxy and
trifluoromethyl.

A further, preferred group of compounds of the formula (I), or more preferably of the formula (IA) or (IB), and the salts thereof, preferably the pharmaceutically acceptable salts thereof, are compounds in which R is
optionally N-mono- or N,N-di-$C_{1-8}$-alkylated carbamoyl-$C_{0-8}$-alkyl,
optionally substituted, preferably by 1-2 substituents independently selected from
$C_{1-8}$-alkoxy,
$C_{1-8}$-alkoxy-$C_{1-8}$-alkoxy,
$C_{1-8}$-alkyl,
cyano,
halogen,
hydroxyl,
oxo,
trifluoromethoxy and
trifluoromethyl.

A further, preferred group of compounds of the formula (I), or more preferably of the formula (IA) or (IB), and the salts thereof, preferably the pharmaceutically acceptable salts thereof, are compounds in which R is
optionally N and/or N' mono-, di- or tri-$C_{1-8}$-alkylated ureido-$C_{1-8}$-alkyl,
optionally substituted, preferably by 1-2 substituents independently selected from
$C_{1-8}$-alkoxy,
$C_{1-8}$-alkoxy-$C_{1-8}$-alkoxy,
$C_{1-8}$-alkyl,
cyano,
halogen,
hydroxyl,
oxo,
trifluoromethoxy and
trifluoromethyl.

A further, preferred group of compounds of the formula (I), or more preferably of the formula (IA) or (IB), and the salts thereof, preferably the pharmaceutically acceptable salts thereof, are compounds in which R is
heterocyclyl-$C_{0-8}$-alkyl,
optionally substituted, preferably by 1-2 substituents independently selected from
$C_{1-8}$-alkoxy,
$C_{1-8}$-alkoxy-$C_{1-8}$-alkoxy,
$C_{1-8}$-alkyl,
cyano,
halogen,
hydroxyl,
oxo,
trifluoromethoxy and
trifluoromethyl.

R is particularly preferably
C$_{0-8}$-alkyl-carbonyl-optionally N-mono-C$_{1-8}$-alkylated amino-C$_{1-8}$-alkyl,
optionally N-mono- or N,N-di-C$_{1-8}$-alkylated carbamoyl-C$_m$-alkyl or
heterocyclyl-C$_{0-8}$-alkyl.

R is very particularly preferably
C$_{0-4}$-alkyl-carbonyl-optionally N-mono-C$_{1-4}$-alkylated amino-C$_{1-4}$-alkyl,
optionally N-mono- or N,N-di-C$_{1-8}$-alkylated carbamoyl-C$_{0-4}$-alkyl, morpholinyl-C$_{0-4}$-alkyl, tetrazolyl-C$_{0-4}$-alkyl or triazolyl-C$_{0-4}$-alkyl.

Prodrug derivatives of the compounds described herein are derivatives thereof which on in vivo use liberate the original compound by a chemical or physiological process. A prodrug may for example be converted into the original compound when a physiological pH is reached or by enzymatic conversion. Possible examples of prodrug derivatives are esters of freely available carboxylic acids, S- and O-acyl derivatives of thiols, alcohols or phenols, the acyl group being defined as herein. Preferred derivatives are pharmaceutically acceptable ester derivatives which are converted by solvolysis in physiological medium into the original carboxylic acid, such as, for example, lower alkyl esters, cycloalkyl esters, lower alkenyl esters, benzyl esters, mono- or disubstituted lower alkyl esters such as lower omega-(amino, mono- or dialkylamino, carboxy, lower alkoxycarbonyl)—alkyl esters or such as lower alpha-(alkanoyloxy, alkoxycarbonyl or dialkylaminocarbonyl)—alkyl esters; conventionally, pivaloyloxymethyl esters and similar esters are used as such.

Because of the close relationship between a free compound, a prodrug derivative and a salt compound, a particular compound in this invention also includes its prodrug derivative and salt form, where this is possible and appropriate.

The compounds of formula (I), preferably of formulae (IA) and (IB), and their pharmaceutically acceptable salts have an inhibitory effect on the natural enzyme renin. The latter passes from the kidneys into the blood and there brings about the cleavage of angiotensinogen to form the decapeptide angiotensin I which is then cleaved in the lung, the kidneys and other organs to the octapeptide angiotensin II. Angiotensin II raises the blood pressure both directly by arterial constriction, and indirectly by releasing the hormone aldosterone, which retains sodium ions, from the adrenals, which is associated with an increase in the extracellular fluid volume. This increase is attributable to the effect of angiotensin II itself or of the heptapeptide angiotensin III formed therefrom as cleavage product. Inhibitors of the enzymatic activity of renin bring about a reduction in the formation of angiotensin I and, as a consequence thereof, the formation of a smaller amount of angiotensin II. The reduced concentration of this active peptide hormone is the direct cause of the blood pressure-lowering effect of renin inhibitors.

The effect of renin inhibitors is detected inter alia experimentally by means of in vitro tests where the reduction in the formation of angiotensin I is measured in various systems (human plasma, purified human renin together with synthetic or natural renin substrate). The following in vitro test of Nussberger et al. (1987) J. Cardiovascular Pharmacol., Vol. 9, pp. 39-44, is used inter alia. This test measures the formation of angiotensin I in human plasma. The amount of angiotensin I formed is determined in a subsequent radioimmunoassay. The effect of inhibitors on the formation of angiotensin I is tested in this system by adding various concentrations of these substances. The IC$_{50}$ is defined as the concentration of the particular inhibitor which reduces the formation of angiotensin I by 50%. The compounds of the present invention show inhibitory effects in the in vitro systems at minimal concentrations of about $10^{-6}$ mol/l to about $10^{-10}$ mol/l.

Illustrative of the invention, the compounds of examples 5 and 9 inhibit the formation of angiotensin I with IC$_{50}$ values in the range of about $0.1 - 10 \cdot 10^{-9}$ mol/l.

Renin inhibitors bring about a fall in blood pressure in salt-depleted animals. Human renin differs from renin of other species. Inhibitors of human renin are tested using primates (marmosets, *Callithrix jacchus*) because human renin and primate renin are substantially homologous in the enzymatically active region. The following in vivo test is employed inter alia: the test compounds are tested on normotensive marmosets of both sexes with a body weight of about 350 g, which are conscious, unrestrained and in their normal cages. Blood pressure and heart rate are measured with a catheter in the descending aorta and are recorded radiometrically. Endogenous release of renin is stimulated by combining a low-salt diet for 1 week with a single intramuscular injection of furosemide (5-(aminosulfonyl)-4-chloro-2-[(2-furanylmethyl)amino]benzoic acid) (5 mg/kg). 16 h after the furosemide injection, the test substances are administered either directly into the femoral artery by means of a hypodermic needle or as suspension or solution by gavage into the stomach, and their effect on blood pressure and heart rate is evaluated. The compounds of the present invention have a blood pressure-lowering effect in the described in vivo test with i.v. doses of about 0.003 to about 0.3 mg/kg and with oral doses of about 0.3 to about 30 mg/kg.

The blood pressure-reducing effect of the compounds described herein can be tested in vivo using the following protocol:

The investigations take place in 5 to 6-week old, male double transgenic rats (dTGR), which overexpress both human angiotensinogen and human renin and consequently develop hypertension (Bohlender J. et al., J. Am. Soc. Nephrol. 2000; 11: 2056-2061). This double transgenic rat strain was produced by crossbreeding two transgenic strains, one for human angiotensinogen with the endogenous promoter and one for human renin with the endogenous promoter. Neither single transgenic strain was hypertensive. The double transgenic rats, both males and females, develop severe hypertension (mean systolic pressure, approximately 200 mm Hg) and die after a median of 55 days if untreated. The fact that human renin can be studied in the rat is a unique feature of this model. Age-matched Sprague-Dawley rats serve as non-hypertensive control animals. The animals are divided into treatment groups and receive test substance or vehicle (control) for various treatment durations. The applied doses for oral administration may range from 0.5 to 100 mg/kg body weight. Throughout the study, the animals receive standard feed and tap water ad libitum. The systolic and diastolic blood pressure, and the heart rate are measured telemetrically by means of transducers implanted in the abdominal aorta, allowing the animals free and unrestricted movement.

The effect of the compounds described herein on kidney damage (proteinuria) can be tested in vivo using the following protocol:

The investigations take place in 4-week old, male double transgenic rats (dTGR), as described above. The animals are divided into treatment groups and receive test substance or vehicle (control) each day for 7 weeks. The applied doses for oral administration may range from 0.5 to 100 mg/kg body weight. Throughout the study, the animals receive standard feed and tap water ad libitum. The animals are placed periodically in metabolism cages in order to determine the 24-hour urinary excretion of albumin, diuresis, natriuresis, and urine osmolality. At the end of the study, the animals are sacrificed and the kidneys and hearts may also be removed for determining the weight and for immunohistological investigations (fibrosis, macrophage/T cell infiltration, etc.).

The bioavailability of the compounds described herein can be tested in vivo using the following protocol:

The investigations take place in pre-catheterized (carotid artery) male rats (300 g±20%) that can move freely throughout the study. The compound is administered intravenously and orally (gavage) in separate sets of animals. The applied doses for oral administration may range from 0.5 to 50 mg/kg body weight; the doses for intravenous administration may range from 0.5 to 20 mg/kg body weight. Blood samples are collected through the catheter before compound administration and over the subsequent 24-hour period using an automated sampling device (AccuSampler, DiLab Europe, Lund, Sweden). Plasma levels of the compound are determined using a validated LC-MS analytical method. The pharmacokinetic analysis is performed on the plasma concentration-time curves after averaging all plasma concentrations across time points for each route of administration. Typical pharmacokinetics parameters to be calculated include: maximum concentration ($C_{max}$), time to maximum concentration ($t_{max}$), area under the curve from 0 hours to the time point of the last quantifiable concentration ($AUC_{0-t}$), area under the curve from time 0 to infinity ($AUC_{0-inf}$), elimination rate constant (K), terminal half-life ($t_{1/2}$), absolute oral bioavailability or fraction absorbed (F), clearance (CL), and Volume of distribution during the terminal phase (Vd).

Five major metabolizing CYP450 enzymes CYP1A2, CYP2C9, CYP2C19, CYP2D6, and CYP3A4 are responsible for more than 95% of the drug metabolizing activity in humans.

The Goals in Evaluating in Vitro Drug Metabolism Are:
(1) to identify all of the major metabolic pathways that affect the test compound and its metabolites, including the identification of the specific enzymes responsible for metabolism and elucidation of the intermediates formed; and
(2) to explore and anticipate the effects of the test drug on the metabolism of other drugs and the effects of other drugs on its metabolism.

The most complete picture for hepatic metabolism can be obtained with intact liver systems (e.g. hepatocytes, microsomes), in which the cofactors are self-sufficient and the natural orientation and location for linked enzymes is preserved.

However, when many compounds have to be tested simultaneously, a simpler screening tool is advantageous. The cDNAs for the common CYP450s have been cloned and the recombinant human enzymatic proteins have been expressed in a variety of cells. Use of these recombinant enzymes provides an excellent way to quickly assess specific enzyme inhibition activities and/or confirm results identified in microsomes.

The metabolic properties (inhibition constants on human cytochrome P450 isoforms) of the compounds described herein can be tested in vivo using the following protocol:

To assess the inhibitory activity towards CYP450 enzymes, the enzymatic reaction is monitored in the presence of different concentrations of test compound (serial dilution) and compared to maximal enzyme activity (control: no test compound). In principle, inhibition can occur by three different mechanisms: (1) competitive inhibition, (2) non-competitive inhibition, and (3) mechanism-based inhibition. In any case, the inhibition strength is dependent on the concentration of test compound. Testing the CYP450 enzyme activity over a test compound concentration range identifies the test compound concentration at which half maximal enzyme inhibition is observed ($IC_{50}$ concentration).

For screening purposes, the inhibitory potential of a test compound can be tested with ready to use kits (CYP450 High Throughput Inhibitor Screening kit, e.g. CYP1A2/CEC, #459500, BD Biosciences, Franklin Lakes, NJ USA), which are available for all of the five above-mentioned major CYP isoforms. In such kits, recombinant human CYP450 isoforms expressed in insect cells are incubated with isoform specific, fluorogenic substrates in the presence of different test compound concentrations. Enzymatic activity converts the fluorogenic substrate into a fluorochrome product, the concentration of which is measured with a fluoro-spectrophotometer. Fluorescence is directly proportional to enzyme activity. In a typical standard assay using the CYP450 High Throughput Inhibitor Screening kit, a compound is tested at 2 nM to 33 μM concentration range in a phosphate buffer (50 mM, pH 7.4) containing a glucose 6-phosphate dehydrogenase/NADP/NADPH regeneration system and a suitable fluorogenic substrate: e.g. 3-cyano-7-ethoxy-coumarin (CYP1A2). As control inhibitors, the following substances can be used: furafylline (CYP1A2), sulfaphenazole (CYP2C9), tranylcypromine (CYP2C19), quinidine (CYP2D6) and ketoconazole (CYP3A4).

The reaction is started by the addition of 2.5 nM (final concentration) CYP450 isozyme, incubated at 37° C. for 15 to 45 minutes, and then terminated by the addition of 187.5 mM tris-hydroxy-aminomethane base/acetonitrile (20/80, v/v).

The amount of generated fluorochrome is then determined by fluorescence spectroscopy with suitable exitation and emission wavelength settings: e.g. 410 nm excitation and 460 nm emission wavelength (CYP1A2).

Alternatively and/or complimentary, assays using human liver microsomes (e.g. BD Biosciences, #452161) in combination with a CYP isoform-specific standard substrate (e.g. midazolam for CYP3A4/5) as described by R. L. Walsky and R. S. Obach in *Validated assay for human cytochrome p450 activities*; Pharmacokinetics, Pharmacodynamics, and Drug Metabolism, Pfizer, Groton, Connecticut; Drug Metabolism and Disposition: (2004)32, 647-660, can be used. To determine whether a test compound inhibits CYP3A enzyme activity, for example, hydroxylation of midazolam by human liver microsomes at varying test compound concentrations is monitored. Hydroxy-midazolam production is directly proportional to enzyme activity and can be determined by liquid chromatography-tandem mass spectrometry. Additionally, the microsomal assay can be run without and with a 15 min pre-incubation of microsomes with test compound prior to the addition of standard substrate. Test compounds or their metabolite(s) that have the potential to irreversibly modify the P450 enzyme will have a stronger inhibitory effect after pre-incubation.

In a typical standard assay using the human liver microsome assay, compounds are tested at 10 nM to 50 μM concentration range in a phosphate buffer (100 mM potassium phosphate, 3.3 mM $MgCl_2$, pH 7.4) containing a NADPH regeneration system (glucose 6-phosphate dehydrogenase, NADP, NADPH) and 10 μM substrate (e.g. midazolam for CYP3A4/5) and 0.1 mg/ml microsomal protein. As control inhibitors, the same substances as described above can be used (e.g. ketoconazole (CYP3A4/5)). If pre-incubation of the compound is desired, all assay components except substrate are mixed and incubated for 15 minutes at 37° C. After that period, substrate is added to the assay mix and then incubation at 37° C. is continued for 15 minutes. Without pre-incubation, all assay components are mixed simultaneously and then incubated at 37° C. for 15 minutes. Termination of the enzymatic reaction is achieved by the addition of a HCOOH/acetonitrile/H$_2$O (4/30/66, v/v/v) solution. Samples are then incubated in the refrigerator (4±2° C.) for 1 h±10 min to increase protein precipitation. Directly before analysis by LC/MSMS, the samples are centrifuged at 3,500 g for 60 min at 4° C. to separate precipitated protein. The supernatant is mixed with acetonitrile/water (50/50, v/v), and then directly analyzed for compound content with LC/MSMS.

Evaluation of the data from either experimental setup is then done as follows: the fraction of remaining activity at a specific compound concentration versus the activity in the control as a function of compound concentration is used to compute IC$_{50}$ values. This is done by fitting a 4-parameter logistic function to the experimental data set.

The compounds of the formula (I), preferably of formulae (IA) and (IB), and their pharmaceutically acceptable salts can be used as medicines, e.g. in the form of pharmaceutical compositions. The pharmaceutical compositions can be administered enterally, such as orally, e.g. in the form of tablets, lacquered tablets, sugar-coated tablets, hard and soft gelatine capsules, solutions, emulsions or suspensions, nasally, e.g. in the form of nasal sprays, rectally, e.g. in the form of suppositories, or transdermally, e.g. in the form of ointments or patches, ophtalmologically, e.g. in the form of solutions, suspensions, ointments, gels, pulmonary, e.g. in the form of pulmonary aerosols or to other mucosal tissues. However, administration is also possible parenterally, such as intramuscularly or intravenously, e.g. in the form of solutions for injection.

Tablets, lacquered tablets, sugar-coated tablets and hard gelatine capsules can be produced by processing the compounds of the formula (I) and their pharmaceutically acceptable salts with pharmaceutically inert inorganic or organic excipients. Excipients of these types which can be used for example for tablets, sugar-coated tablets and hard gelatine capsules are lactose, maize starch or derivatives thereof, talc, stearic acid or salts thereof etc.

Excipients suitable for soft gelatine capsules are, for example, vegetable oils, waxes, fats, semisolid and liquid polyols etc.

Excipients suitable for producing solutions and syrups are, for example, water, polyols, sucrose, invert sugar, glucose etc.

Excipients suitable for solutions for injection are, for example, water, alcohols, polyols, glycerol, vegetable oils, bile acids, lecithin etc.

Excipients suitable for suppositories are, for example, natural or hardened oils, waxes, fats, semiliquid or liquid polyols etc.

The pharmaceutical compositions may in addition comprise preservatives, solubilizers, viscosity-increasing substances, stabilizers, wetting agents, emulsifiers, sweeteners, colorants, aromatizers, salts to alter the osmotic pressure, buffers, coating agents or antioxidants. They may also comprise other substances of therapeutic value.

The present invention further provides the use of the compounds of the formula (I), preferably of formulae (IA) and (IB), and their pharmaceutically acceptable salts in the treatment, for the delay of progression or for the prevention of high blood pressure, heart failure, glaucoma, myocardial infarction, renal failure, diabetic nephropathy and restenoses.

The present invention also provides a method in the treatment, for the delay of progression or for the prevention of high blood pressure, heart failure, glaucoma, myocardial infarction, renal failure, diabetic nephropathy or restenoses comprising administering a therapeutically effective amount of the compounds of the formula (I), preferably of formulae (IA) and (IB), and their pharmaceutically acceptable salts to a subject in need thereof.

The subject/patient may be an animal, mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

The compounds of the formula (I), preferably of formulae (IA) and (IB), and their pharmaceutically acceptable salts can also be administered in combination with one or more agents having cardiovascular activity, e.g. alpha- and beta-blockers such as phentolamine, phenoxybenzamine, prazosin, terazosin, tolazine, atenolol, metoprolol, nadolol, propranolol, timolol, carteolol etc.; vasodilators such as hydralazine, minoxidil, diazoxide, nitroprusside, flosequinan etc.; calcium antagonists such as amrinone, bencyclan, diltiazem, fendiline, flunarizine, nicardipine, nimodipine, perhexiline, verapamil, gallopamil, nifedipine etc.; ACE inhibitors such as cilazapril, captopril, enalapril, lisinopril etc.; potassium activators such as pinacidil; anti-serotoninergics such as ketanserine; thromboxane synthetase inhibitors; neutral endopeptidase inhibitors (NEP inhibitors); angiotensin II antagonists; and diuretics such as hydrochlorothiazide, chlorothiazide, acetazolamide, amiloride, bumetanide, benzthiazide, ethacrynic acid, furosemide, indacrinone, metolazone, spironolactone, triamterene, chlorthalidone etc.; sympatholytics such as methyldopa, clonidine, guanabenz, reserpine; and other agents suitable for the treatment of high blood pressure, heart failure or vascular disorders associated with diabetes or renal disorders such as acute or chronic renal failure in humans and animals. Such combinations can be used separately or in products which comprise a plurality of components.

Further substances which can be used in combination with the compounds of formula (I), preferably of formulae (IA) and (IB), are the compounds of classes (i) to (ix) on page 1 of WO 02/40007 (and the preferences and examples detailed further therein) and the substances mentioned on pages 20 and 21 of WO 03/027091.

The dosage may vary within wide limits and must of course be adapted to the individual circumstances in each individual case. In general, a daily dose appropriate for oral administration ought to be from about 3 mg to about 3 g, preferably about 10 mg to about 1 g, e.g. approximately 300 mg per adult person (70 kg), divided into preferably 1-3 single doses, which may be for example of equal size, although the stated upper limit may also be exceeded if this proves to be indicated, and children usually receive a reduced dose appropriate for their age and body weight.

The compounds of the formula (I), preferably of formulae (IA) and (IB), and their pharmaceutically acceptable salts can also be administered with one or several varying dosing intervals, as long as the intended therapeutic effect is sustained or as long as further therapeutic intervention is not required.

EXAMPLES

The examples which follow illustrate the present invention. All temperatures are reported in degrees Celsius, pressures in mbar. Unless stated otherwise, the reactions take place at RT. The abbreviation "Rf=xx (A)" means, for example, that the Rf value xx is obtained in the solvent system A. The ratio of the solvents relative to one another is always reported in parts by volume. Chemical names of end products and intermediates were obtained with the aid of the program AutoNom 2000 (Automatic Nomenclature).

HPLC gradient on Hypersil BDS C-18 (5 µm); column: 4×125 mm

I 90% $H_2O$*/10% $CH_3CN$* to 0% $H_2O$*/100% $CH_3CN$* in 5 min+2.5 min (1.5 ml/min)

II 95% $H_2O$*/5% $CH_3CN$* to 0% $H_2O$*/100% $CH_3CN$* in 30 min+5 min (0.8 ml/min)

* contains 0.1% trifluoroacetic acid

The following abbreviations are used:

Rf ratio of distance which a substance travels to distance of the eluent front from the start point in thin layer chromatography Rt retention time of a substance in HPLC (in minutes)

m.p. melting point (temperature)

The following abbreviations are used:

AcOH acetic acid
n-BuLi n-butyllithium
t-BuOH tert-butanol
$CH_2Cl_2$ dichloromethane
$CHCl_3$ chloroform
$CH_3CN$ acetonitrile
$Cs_2CO_3$ caesium carbonate
Cy cyclohexane
DCC dicyclohexylcarbodiimide
DIBAL diisobutylaluminium hydride
DMA dimethylacetamide
4-DMAP 4-dimethylamino pyridine
DME 1,2-dimethoxyethane
DMF N,N-dimethylformamide
DMPU 1,3-dimethyl-3,4,5,6-tetrahydro-2(1H)-pyrimidinone
dppf 1,1'-bis(diphenylphosphino)-ferrocene [12150-46-8]
EDC.HCl N-ethyl-N'-(3-dimethylaminopropyl)carbodiimide hydrochloride [25952-53-8]
$Et_3N$ triethylamine
$Et_2O$ diethylether
EtOAc ethyl acetate
EtOH ethanol
h hour
HCl hydrochloric acid
$H_2O$ water
$K_2CO_3$ potassium carbonate
$LiBH_4$ lithium borohydride
LiCl lithium chloride
MeI methyl iodide
MeOH methanol
min minute(s)
m.p. melting point (temperature)
$N_2$ nitrogen
$Na_2CO_3$ sodium carbonate
NaH sodium hydride
$NaHCO_3$ sodium bicarbonate
$Na_2HPO_4$ di-sodium hydrogen phosphate
NaOH sodium hydroxide
$Na_2SO_4$ sodium sulfate
$NH_3$ ammonia
$NH_4Br$ ammonium bromide
$NH_4Cl$ ammonium chloride
$NH_4OH$ ammonium hydroxide
$Pd_2(dba)_3$ tris(dibenzylideneacetone)dipalladium [51364-51-3]
$Pd(PPh_3)_4$ tetrakis-triphenylphosphine palladium(0)
$P(tert-Bu)_3$ tri-tert-butylphosphine
Ra/Ni Raney-nickel Rf ratio of distance which a substance travels to distance of the eluent front from the start point in thin layer chromatography Rt retention time of a substance in HPLC (in minutes)

RT room temperature corresponding to about 23° C.

TBACl tetrabutyl ammonium chloride
TBAF tetrabutyl ammonium fluoride
TBAI tetrabutyl ammonium iodide
TBME tert-butyl methyl ether
TFA trifluoroacetic acid
THF tetrahydrofuran
TMS trimethylsilyl General Procedure A: (N-Tos-Deprotection)

To a stirred solution of 0.09 mmol "tosylamide" in 10 ml of MeOH are added 0.44 mmol sodiumdihydrogenphosphate and 0.90 mmol of sodium amalgam (10% Na) at RT. The reaction mixture is stirred for 2-18 h, diluted with water and extracted with EtOAc. The organic phases are combined, washed with brine and dried over $Na_2SO_4$. The solvent is concentrated under reduced pressure and the residue is purified by flash chromatography ($SiO_2$ 60 F) to afford the title compound.

General Procedure B: (N-p-Methoxyphenyl Deprotection)

To a stirred solution of 0.5 mmol "p-methoxyanilin" in 10 ml of $CH_3CN/H_2O$ (1:1) is added a solution of 1.43 mol of ceric ammonium nitrate in 5.0 ml of $H_2O$ at 0° C. The mixture is stirred for 30 min, followed by addition of 1.0 g of sodium sulfite. After additional 30 min, the mixture is diluted with $H_2O$ and extracted with TBME. The organic phase is dried and concentrated under reduced pressure. The residue is purified by flash chromatography ($SiO_2$ 60 F) to afford the title compound.

General Procedure C: ($BH_3$-Reduction)

To a stirred solution of 1.0 mmol of "lactam" in 3 ml of THF is admixed with 2-4 mmol of borane tetrahydrofuran (1 M in THF) and heated to 50° C. for 2-8 h. The reaction mixture is quenched by addition of 10 ml of MeOH and concentrated under reduced pressure. The title compound is obtained from the residue by means of flash chromatography ($SiO_2$ 60 F).

General Procedure D: (Amide-Formation)

To a stirred solution of 1.0 mmol of "acid" and "1.0 mmol of "amin" in 20 ml of $CH_2Cl_2$ are added 5.0 mmol of $Et_3N$ and 1.0 mmol of tri-propylphosphonic acid cyclic anhydride [68957-94-8] (50% in ethyl acetate) at RT. The reaction mixture is stirred for 1-3 h, diluted with $CH_2Cl_2$, washed with 1N aqueous HCl and brine. The organic phases are combined, dried over $Na_2SO_4$ and the solvent is concentrated under reduced pressure. The residue is purified by flash chromatography ($SiO_2$ 60 F) to afford the title compound.

General Procedure E: (Hydrogenation)

To a stirred solution of 1.0 mmol of "substrate" in 15 ml of THF are added 100-200 mg Pd/C 10% and the reaction mixture is hydrogenated at 15-20° C. The reaction mixture is filtered and concentrated under reduced pressure. The residue is purified by flash chromatography ($SiO_2$ 60 F) to afford the title compound.

General Procedure F: (Mesylation)

To a stirred solution of 1.0 mmol of "alcohol" in 10 ml of $CH_2Cl_2$ are added 5 mmol of $Et_3N$ and 2 mmol of methanesulfonyl chloride at 0° C. The reaction mixture is allowed to stir for 1 h, diluted with $CH_2Cl_2$, washed with 1N aqueous HCl, and dried over $Na_2SO_4$. The solvent is concentrated under reduced pressure and the residue is purified by flash chromatography ($SiO_2$ 60 F) to afford the title compound or is directly used in the next step without any further purification.

General Procedure G: (Substitution of Mesylate by Nitrile)

A solution of 0.5 mmol of "mesylate" and 5.5 mmol of sodium cyanide in 3 ml of DMSO is stirred at 60° C. for 20 h. Subsequently, the mixture is diluted with EtOAc and washed with brine. The aqueous phase is extracted with EtOAc (2×). The combined organic phases are dried with Na$_2$SO$_4$ and concentrated by evaporation. The crude title compound is obtained from the residue.

General Method H: (Nitrile Hydrolysis)

A suspension of 3.5 mmol of "nitrile" in 55 ml of ethanol and 55 ml of 2M aqueous NaOH is stirred at 80° C. for 21 h. Subsequently, the mixture is concentrated and the residue is adjusted to pH 2-3 with 1M aqueous HCl. The mixture is extracted with EtOAc (2×). The residue is diluted with CH$_2$Cl$_2$, and washed with 1M aqueous HCl and finally with brine. The combined organic phases are dried over Na$_2$SO$_4$ and concentrated by evaporation. The crude title compound is obtained from the residue.

General Method I: (Alcohol Alkylation)

A solution of 235 mmol of "alcohol" in 800 ml of THF are added 239 mmol of sodium hydride (60% dispersion in oil) in portions. The reaction mixture is stirred for 30 min and 235 mmol of "halide" and 282 mmol of TBAI are added. The reaction is stirred at 70° C. for 5 h. Ice-water is added and the mixture is extracted with EtOAc (2×). The combined organic phases are washed with brine, dried over Na$_2$SO$_4$ and concentrated by evaporation. The title compound is obtained from the residue by means of flash chromatography (SiO$_2$ 60 F).

General Method J: (Methoxyphenol Demethylation)

A solution of 3.99 mmol of "methoxyphenol" in 35 ml of DMF is treated with 39.9 mmol of sodium ethanethiolate and the resulting suspension is heated at 120° C. for 21 h. The reaction mixture is cooled to 0° C. and adjusted to pH 2 using 2M aqueous HCl. The mixture is diluted with water and extracted with TBME (2×). The combined organic phases are dried using Na$_2$SO$_4$ and evaporated. The title compound is obtained from the residue by means of flash chromatography (SiO$_2$ 60 F).

General Method K: (Phenol Alkylation)

A suspension of 1.0 mmol of "phenol", 1.0-1.5 mmol of "tosylate" or "bromide", 1.5 mmol of caesium carbonate in 2 ml of acetonitrile is stirred at 80° C. for 2 h. The reaction mixture is cooled, poured into water and extracted with EtOAc (2×). The organic phases are washed with brine, dried with Na$_2$SO$_4$ and evaporated. The title compound is obtained from the residue by flash chromatography (SiO$_2$ 60 F).

Example 1

6-{(3R,4R,6S)-4-[4-((R)-2-Ethoxy-propoxymethyl)-phenyl]-6-[(R)-2-(1H-tetrazol-5-yl) -propyl]-piperidin-3-yloxymethyl}-4-(3-methoxy-propyl)-3,4-dihydro-2H-benzo[1,4]oxazine According to the general procedure A, 1.0 mmol of 6-[(3R,4R,6S)-4-[4-((R)-2-ethoxy -propoxymethyl)-phenyl]-6-[(R)-2-(1H-tetrazol-5-yl)-propyl]-1-(toluene-4-sulfonyl) -piperidin-3-yloxymethyl]-4-(3-methoxy-propyl)-3,4-dihydro-2H-benzo[1,4]oxazine is reacted to afford the title compound, which is identified based on its Rf value.

The starting materials are prepared as follows:

a) 6-[(3R,4R,6S)-4-[4-((R)-2-Ethoxy-propoxymethyl)-phenyl]-6-[(R)-2-(1H-tetrazol-5-yl) -propyl]-1-(toluene-4-sulfonyl)-piperidin-3-yloxymethyl]-4-(3-methoxy-propyl) -3,4-dihydro-2H-benzo[1,4]oxazine To a stirred solution of 1.0 mmol of (R)-3-[(2S,4R,5R)-4-[4-((R)-2-ethoxy-propoxy-methyl) -phenyl]-5-[4-(3-methoxy-propyl)-3,4-dihydro-2H-benzo[1,4]oxazin-6-yl-methoxy]-1-(toluene-4-sulfonyl)-piperidin-2-yl]-2-methyl-propionitrile and 0.3 mmol of dibutyltin oxide in 10 ml of toluene are added 40.0 mmol of trimethylsilylazide. The reaction mixture is heated to 125° C. overnight, concentrated under reduced pressure and the residue is purified by flash chromatography (SiO$_2$ 60 F) to afford the title compound which is identified based on its Rf value.

b) (R)-3-[(2S,4R,5R)-4-[4((R)-2-Ethoxy-propoxymethyl)-phenyl]-5-[4-(3-methoxy-propyl) -3,4-dihydro-2H-benzo[1,4]oxazin-6-ylmethoxy]-1-(toluene-4-sulfonyl) -piperidin-2-yl]-2-methyl-propionitrile The title compound is prepared according to the general procedure G starting from 1.0 mmol of methanesulfonic acid (S)-2-[(2R,4R,5R)-4-[4-((R)-2-ethoxy-propoxy-methyl) -phenyl]-5-[4-(3-methoxy-propyl)-3,4-dihydro-2H-benzo[1,4]oxazin-6-ylmethoxy]-1-(toluene-4-sulfonyl)-piperidin-2-yl]-1-methyl-ethyl ester and is identified based on its Rf value.

c) Methanesulfonic acid (S)-2-[(2R,4R,5R)-4-[4-((R)-2-Ethoxy-propoxymethyl) -phenyl]-5-[4-(3-methoxy-propyl)-3,4-dihydro-2H-benzo[1,4]oxazin-6-ylmethoxy]-1-(toluene-4-sulfonyl)-piperidin-2-yl]-1-methyl-ethyl ester The title compound is prepared according to the general procedure F starting from 1.0 mmol of (S)-1-[(2R,4R,5R)-4-[4-((R)-2-ethoxy-propoxymethyl)-phenyl]-5-[4-(3-meth-oxy-propyl) -3,4-dihydro-2H-benzo[1,4]oxazin-6-ylmethoxy]-1-(toluene-4-sulfonyl) -piperidin-2-yl]-propan-2-ol and is identified based on its Rf value.

d) (S)-1-[(2R,4R,5R)-4-[4-((R)-2-Ethoxy-propoxymethyl)-phenyl]-5-[4-(3-methoxy-propyl) -3,4-dihydro-2H-benzo[1,4]oxazin-6-ylmethoxy]1-(toluene-4-sulfonyl) -piperidin-2-yl]-phenyl-2-ol To a stirred solution of 1.0 mmol of 1-[(2R,4R,5R)-4-[4-((R)-2-ethoxy-propoxymethyl) -phenyl]-5-[4-(3-methoxy-propyl)-3,4-dihydro-2H-benzo[1,4]oxazin-6-ylmethoxy]-1-(toluene-4-sulfonyl)-piperidin-2-yl]-phenyl-2-one in 10 ml of THF are added 2.0 mmol of borane-tetrahydrofuran complex (1M in THF) at RT. The reaction mixture is stirred for 3 h, quenched with 60 ml of MeOH and concentrated under reduced pressure. The resulting diastereomeric mixture is separated by flash chromatography (SiO$_2$ 60 F) to afford the title compound which is identified based on its Rf value.

e) 1-[(2R,4R,5R)-4-[4-((R)-2-Ethoxy-propoxymethyl)-phenyl]-5-[4-(3-methoxy-propyl) -3,4-dihydro-2H-benzo[1,4]oxazin-6-ylmethoxy]-1-(toluene-4-sulfonyl) -piperidin-2-yl]-phenyl-2-one To a stirred solution of 1.0 mmol of N-methoxy-2-[(2R,4R,5R)-4-[4-((R)-2-ethoxy-propoxymethyl) -phenyl]-5-[4-(3-methoxy-propyl)-3,4-dihydro-2H-benzo[1,4]oxazin-6-ylmethoxy]-1-(toluene-4-sulfonyl)-piperidin-2-yl]-N-methyl-acetamide in 10 ml of THF are added 1.2 mmol of methyl magnesium bromide (3M in THF) at 0° C. The reaction mixture is stirred for 1 h, diluted with an aqueous solution of 1N potassium hydrogen sulfate, extracted with TBME. The organic phases are combined and dried over Na$_2$SO$_4$. The residue is purified by flash chromatography (SiO$_2$ 60 F) to afford the title compound which is identified based on its Rf value.

f) N-Methoxy-2-[(2R,4R,5R)-4-[4-((R)-2-Ethoxy-propoxymethyl)-phenyl]-5-[4-(3-methoxy-propyl) -3,4-dihydro-2H-benzo[1,4]oxazin-6-ylmethoxy]-1-(toluene-4-sulfonyl) -piperidin-2-yl]-N-methyl-acetamide According to general procedure D, 1.0 mmol of [(2R,4R,5R)-4-[4-((R)-2-ethoxy-propoxymethyl) -phenyl]-5-[4-(3-methoxy-propyl)-3,4-dihydro-2H-benzo[1,4]oxazin-6-yl-methoxy]-1-(toluene-4-sulfonyl)-piperidin-2-yl]-acetic acid are reacted with N,O-dimethylhydroxylamine hydrochloride to afford the title compound which is identified based on its Rf value.

g) [(2R,4R,5R)-4-[4-((R)-2-Ethoxy-propoxymethyl)-phenyl]-5-[4-(3-methoxy-propyl) -3,4-dihydro-2H-benzo[1,4]oxazin-6-ylmethoxy]-1-(toluene-4-sulfonyl)-piperidin-2-yl]-acetic acid The title compound is prepared according to general procedure H starting from 1.0 mmol of [(2S,4R,5R)-4-[4-((R)-2-ethoxy-propoxymethyl)-phenyl]-5-[4-(3-methoxy-propyl) -3,4-dihydro-2H-benzo[1,4]oxazin-6-ylmethoxy]-1-(toluene-4-sulfonyl) -piperidin-2-yl]-acetonitrile. Rf=0.23 (EtOAc); Rt=5.09 (gradient I).

h) [(2S,4R,5R)-4-[4-((R)-2-Ethoxy-propoxymethyl)-phenyl]-5-[4-(3-methoxy-propyl) -3,4-dihydro-2H-benzo[1,4]oxazin-6-ylmethoxy]-1-(toluene-4-sulfonyl)-piperidin-2-yl]-acetonitrile The title compound is prepared according to general procedure G starting from 1.0 mmol of methanesulfonic acid (2S,4R,5R)-4-[4-((R)-2-ethoxy-propoxymethyl) -phenyl]-5-[4-(3-methoxy-propyl)-3,4-dihydro-2H-benzo[1,4]oxazin-6-ylmethoxy]-1-(toluene-4-sulfonyl)-piperidin-2-ylmethyl ester. Rt=5.47 (gradient I).

i) Methanesulfonic acid (2S,4R,5R)-4-[4-((R)-2-Ethoxy-propoxymethyl)-phenyl]-5-[4-(3-methoxy-propyl)-3,4-dihydro-2H-benzo[1,4]oxazin-6-ylmethoxy]-1-(toluene-4-sulfonyl) -piperidin-2-ylmethyl ester The title compound is prepared according to general procedure F starting from 1.0 mmol of [(2S,4R,5R)-4-[4-((R)-2-ethoxy-propoxymethyl)-phenyl]-5-[4-(3-methoxy-propyl) -3,4-dihydro-2H-benzo[1,4]oxazin-6-ylmethoxy]-1-(toluene-4-sulfonyl) -piperidin-2-yl]-methanol. Rt=5.44 (gradient I).

j) [(2S,4R,5R)-4-[4-((R)-2-Ethoxy-propoxymethyl)-phenyl]-5-[4-(3-methoxy-propyl) -3,4-dihydro-2H-benzo[1,4]oxazin-6-ylmethoxy]-1-(toluene-4-sulfonyl)-piperidin-2-yl]-methanol To a stirred solution of 1.0 mmol of 6-[(3R,4R,6S)-4-[4-((R)-2-ethoxy-propoxymethyl) -phenyl]-1-(toluene-4-sulfonyl)- 6-triisopropylsilanyloxymethyl-piperidin-3-yloxymethyl]-4-(3-methoxy-propyl)-3,4-dihydro-2H-benzo[1,4] oxazine in 10 ml of THF are added 2.5 mmol of a 1N solution of TBAF in THF at RT. The reaction mixture is stirred for 2 h at RT, diluted with water and extracted with TBME. The combined organic phases are dried over Na$_2$SO$_4$ and concentrated under reduced pressure. The crude product is purified by flash chromatography (SiO$_2$ 60 F) to afford the title compound as a yellow oil. Rt=5.44 (gradient I).

k) 6-[(3R,4R,6S)-4-[4-((R)-2-Ethoxy-propoxymethyl)-phenyl]-1-(toluene-4-sulfonyl) -6-triisopropylsilanyloxymethyl-piperidin-3-yloxymethyl]-4-(3-methoxy-propyl)-3,4-dihydro-2H-benzo[1,4]oxazine To a solution of 1.0 mmol of 6-[(3R,4R,6S)-4-(4-chloromethyl-phenyl)-1-(toluene-4-sulfonyl) -6-triisopropylsilanyloxymethyl-piperidin-3-yloxymethyl]-4-(3-methoxy-propyl) -3,4-dihydro-2H-benzo[1,4]oxazine, 1.5 mmol of (R)-2-ethoxy-propan-1-ol and 0.1.0 mmol of TBAI in 5 ml of DMF are added 1.65 mmol of sodium hydride (55% in dispersion oil) at 0° C. The reaction mixture is allowed to warm to RT and stirred overnight, diluted with water, extracted with TBME and the organic phase is dried over Na$_2$SO$_4$. The organic phase is concentrated under reduced pressure and the residue is purified by flash chromatography (SiO$_2$ 60 F) to afford the title compound as a pale yellow oil. Rf=0.20 (EtOAc/heptane 1:2).

l) 6-[(3R,4R,6S)-4-(4-Chloromethyl-phenyl)-1-(toluene-4-sulfonyl)-6-triisopropylsilanyloxymethyl-piperidin-3-yloxymethyl]-4-(3-methoxy-propyl) -3,4-dihydro-2H-benzo[1,4]oxazine To a solution of 1.0 mmol of {4-[(2S,4R,5R)-5-[4-(3-methoxy-propyl)-3,4-dihydro-2H-benzo[1,4]oxazin-6-ylmethoxy]-1-(toluene-4-sulfonyl)-2-triisopropylsilanyloxymethyl -piperidin-4-yl]-phenyl}-methanol [911707-31-8], 1.2 mmol of Et$_3$N and 0.1.0 mmol of TBACl in 10 ml of CH$_2$Cl$_2$ are added 1.1 mmol of methanesulfonyl chloride at 0° C. The reaction mixture is allowed to warm to RT and stirred overnight, diluted with CH$_2$Cl$_2$, washed with saturated aqueous NaHCO$_3$, water and brine. The organic phase is dried over Na$_2$SO$_4$ and is concentrated under reduced pressure to afford the title compound as a yellow oil. Rf=0.77 (EtOAc/heptane 2:1).

m) (R)-2-Ethoxy-propan-1-ol

To a solution of 1.0 mmol of (R)-2-ethoxy-propionic acid methyl ester in 2 ml of Et$_2$O at 0° C. are added 1.55 mmol of lithium borohydride. The reaction mixture is stirred at 0° C. for 1 h, then at RT for 18 h. The solution is then slowly poured into ice-cold saturated NH$_4$Cl, and the mixture is stirred vigorously for 3 h. The aqueous layer is extracted with Et$_2$O (2×), and with CH$_2$Cl$_2$ (7×). The combined organic extracts are dried over Na$_2$SO$_4$, concentrated under reduced pressure, and purified by flash chromatography to afford the title compound as a pale yellow oil. Rf=0.27 (CH$_2$Cl$_2$/Et$_2$O 3:1).

n) (R)-2-Ethoxy-propionic acid methyl ester

To a solution of 1.0 mmol of methyl (R)-lactate [17392-83-5] and 2.0 mmol of ethyl iodide in 1 ml Et$_2$O, protected from light, at RT, are added 2.0 mmol of silver oxide. The reaction mixture is stirred at RT for 20 h. Ethyl iodide (1.0 mmol) and silver oxide (1.0 mmol) are added, and the mixture is stirred at RT for a further 24 h, before being filtered through hyflo, washing with Et$_2$O, then CH$_2$Cl$_2$. The filtrate is concentrated under reduced pressure and purified by flash chromatography (SiO$_2$ 60 F) to afford the title compound as a pale yellow oil. Rf=0.39 (pentane/Et$_2$O 4:1).

Example 2

N,N-Diethyl-2-{(2R,4R,5R)-4-[4-((R)-2-Ethoxy-propoxymethyl)-phenyl]-5-[4-(3-methoxy-propyl) -3,4-dihydro-2H-benzo[1,4]oxazin-6-ylmethoxy]-piperidin-2-yl}-acetamide According to the general procedure A, 1.0 mmol of N,N-diethyl-2-[(2R,4R,5R)-4-[4-((R)-2-ethoxy-propoxymethyl)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-acetamide is reacted, to afford the title compound, which is identified based on its Rf value.

The starting material is prepared as follows:

a) N,N-Diethyl-2-[(2R,4R,5R)-4-[4-((R)-2-Ethoxy-propoxymethyl)-phenyl]-5-[4-(3-methoxy-propyl) -3,4-dihydro-2H-benzo[1,4]oxazin-6-ylmethoxy]-1-(toluene-4-sulfonyl) -piperidin-2-yl]-acetamide According to general procedure D, 1.0 mmol of [(2R,4R,5R)-4-[4-((R)-2-ethoxy-propoxymethyl) -phenyl]-5-[4-(3-methoxy-propyl)-3,4-dihydro-2H-benzo[1,4]oxazin-6-ylmethoxy]-1-(toluene-4-sulfonyl)-piperidin-2-yl]-acetic acid (example 1g) are reacted with diethylamine to afford the title compound, which is identified based on its Rf value.

Example 3

N-((S)-2-{(2S,4R,5R)-4-[4-((R)-2-Ethoxy-propoxymethyl)-phenyl]-5-[4-(3-methoxy-propyl) -3,4-dihydro-2H-benzo[1,4]oxazin-6-ylmethoxy]-piperdin-2-yl}-1-methyl-ethyl) -acetamide

According to the general procedure A, 1.0 mmol of N-{(S)-2-[(2S,4R,5R)-4-[4-((R)-2-ethoxy-propoxymethyl)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-1-methyl-ethyl}-acetamide is reacted, to afford the title compound, which is identified based on its Rf value.

The starting materials are prepared as follows:

a) N-{(S)-2-[(2S,4R,5R)-4-[4-((R)-2-Ethoxy-propoxymethyl)-phenyl]-5-[4-(3-methoxy-propyl) -3,4-dihydro-2H-benzo[1,4]oxazin-6-ylmethoxy]-1-(toluene-4-sulfonyl) -piperidin-2-yl]-1-methyl-ethyl}-acetamide and
N-{(R)-2-[(2S,4R,5R)-4-[4-((R)-2-Ethoxy-propoxymethyl)-phenyl]-5-[4-(3-methoxy-propyl) -3,4-dihydro-2H-benzo[1,4]oxazin-6-ylmethoxy]-1-(toluene-4-sulfonyl) -piperidin-2-yl]-1-methyl-ethyl}-acetamide To a solution of 1.0 mmol of (R and S)-2-[(2S,4R,5R)-4-[4(R)-2-ethoxy-propoxy-methyl) -phenyl]-5-[4-(3-methoxy-propyl)-3,4-dihydro-2H-benzo[1,4]oxazin-6-ylmethoxy]-1-(toluene-4-sulfonyl)-piperidin-2-yl]-1-methyl-ethylamine and 4.0 mmol of Et$_3$N in 25 ml of CH$_2$Cl$_2$ are added 2.0 mmol of acetyl chloride at 0° C. and the resulting mixture is stirred for 1 h. The reaction mixture is diluted with water and extracted with CH$_2$Cl$_2$. The organic phases are combined, dried over Na$_2$SO$_4$ and concentrated under reduced pressure. The resulting diastereomeric mixture is separated by flash chromatography (SiO$_2$ 60 F) to afford the title compounds, which are identified based on their Rf values.

b) (R and S)-2-[(2S,4R,5R)-4-[4-((R)-2-Ethoxy-propoxymethyl)-phenyl]-5-[4-(3-methoxy-propyl) -3,4-dihydro-2H-benzo[1,4]oxazin-6-ylmethoxy]-1-(toluene-4-sulfonyl) -piperidin-2-yl]-1-methyl-ethylamine According to general procedure E, 1.0 mmol of (R and S)-6-[(3R,4R,6S)-6-(2-azido-propyl) -4-[4-((R)-2-ethoxy-propoxymethyl)-phenyl]-1-(toluene-4-sulfonyl)-piperidin-3-yloxymethyl]-4-(3-methoxy-propyl)-3,4-dihydro-2H-benzo[1,4]oxazine are hydrogenated in 20 ml of MeOH to afford the title compound as a diastereomeric mixture, which is identified based on its Rf value.

c) (R and S)-1-[(3R,4R,6S)-6-(2-Azido-propyl)-4-[4-((R)-2-ethoxy-propoxymethyl) -phenyl]-1-(toluene-4-sulfonyl)-piperidin-3-yloxymethyl]-4-(3-methoxy-propyl)-3,4-dihydro-2H-benzo[1,4]oxazine To a solution of 1.0 mmol of methanesulfonic acid (R and S)-2-[(2S,4R,5R)-4-[4-((R) -2-ethoxy-propoxymethyl)-phenyl]-5-[4-(3-methoxy-propyl)-3,4-dihydro-2H-benzo[1,4] oxazin-6-ylmethoxy]-1-(toluene-4-sulfonyl)-piperidin-2-yl]-1-methyl-ethyl ester in 5.0 ml of DMPU is added 10.0 mmol of sodium azide and the mixture is heated to 80° C. overnight. The reaction mixture is diluted with water and extracted with TBME. The organic phases are combined, concentrated under reduced pressure and purified by flash chromatography (SiO$_2$ 60 F) to afford the title compound, which is identified based on its Rf value.

d) Methanesulfonic acid (R and S)-2-[(2S,4R,5R)-4-[4-((R)-2-ethoxy-propoxymethyl) -phenyl]-5-[4-(3-methoxy-propyl)-3,4-dihydro-2H-benzo[1,4]oxazin-6-ylmethoxy]-1-(toluene-4-sulfonyl)-piperidin-2-yl]-1-methyl-ethyl ester According to general procedure F, 1.0 mmol of (R and S)-1-[(2S,4R,5R)-4-[4-((R)-2-ethoxy-propoxymethyl)-phenyl]-5-[4-(3-methoxy-propyl)-3,4-dihydro-2H-benzo[1,4] oxazin-6-ylmethoxy]-1-(toluene-4-sulfonyl)-piperidin-2-yl]-propan-2-ol is reacted, to afford the title compound, which is identified based on its Rf value.

e) (R and S)-1-[(2S,4R,5R)-4-[4-((R)-2-Ethoxy-propoxymethyl)-phenyl]-5-[4-(3-methoxy-propyl) -3,4-dihydro-2H-benzo[1,4]oxazin-6-ylmethoxy]-1-(toluene-4-sulfonyl) -piperidin-2-yl]-propan-2-ol To a stirred solution of 1.0 mmol [(2S,4R,5R)-4-[4-((R)-2-ethoxy-propoxymethyl) -phenyl]-5-[4-(3-methoxy-propyl)-3,4-dihydro-2H-benzo[1,4]oxazin-6-ylmethoxy]-1-(toluene-4-sulfonyl)-piperidin-2-yl]-acetaldehyde in 10 ml of THF are added 2.0 mmol of methyl magnesium bromide (3M in THF) at 0° C. The reaction mixture is allowed to warm to RT and stirred for 1 h, diluted with an aqueous solution of 1N potassium hydrogen sulfate and extracted with TBME. The organic phases are combined and dried over Na$_2$SO$_4$. The residue is purified by flash chromatography (SiO$_2$ 60 F) to afford the title compound, which is identified based on its Rf value.

f) [(2S,4R,5R)-4-[4-((R)-2-Ethoxy-propoxymethyl)-phenyl]-5-[4-(3-methoxy-propyl) -3,4-dihydro-2H-benzo[1, 4]oxazin-6-ylmethoxy]-1-(toluene-4-sulfonyl)-piperidin-2-yl]-acetaldehyde To 1.0 mmol of [(2S,4R,5R)-4-[4-((R)-2-ethoxy-propoxymethyl)-phenyl]-5-[4-(3-methoxy-propyl) -3,4-dihydro-2H-benzo[1,4]oxazin-6-ylmethoxy]-1-(toluene-4-sulfonyl) -piperidin-2-yl]-acetonitrile (example 1h) in 10 ml of toluene are added 1.2 mmol of DIBAL (1.5M in toluene) at −40° C. The reaction mixture is stirred for 4 h at −40° C. to −20° C. and poured into 1N HCl. The organic phase is separated, washed with brine, dried over Na$_2$SO$_4$ and concentrated under reduced pressure. The residue is purified by flash chromatography (SiO$_2$ 60 F) to afford the title compound, which is identified based on its Rf value.

According to the processes described for example 3, the following example is prepared in an analogous manner:

4 N-((R)-2-{(2S,4R,5R)-4-[4-((R)-2-Ethoxy-propoxymethyl)-phenyl]-5-[4-(3-methoxy-propyl) -3,4-dihydro-2H-benzo[1,4]oxazin-6-ylmethoxy]-piperdin-2-yl}-1-methyl-ethyl)-acetamide starting from 1.0 mmol of N-{(R)-2-[(2S,4R,5R)-4-[4-((R)-2-Ethoxy-propoxymethyl) -phenyl]-5-[4-(3-methoxy-propyl)-3,4-dihydro-2H-benzo[1,4]oxazin-6-ylmethoxy]-1-(toluene-4-sulfonyl)-piperidin-2-yl]-1-methyl-ethyl}-acetamide.

Example 5

3-{(2S,4R,5R)-4-[4-((R)-2-Ethoxy-propoxymethyl)-phenyl]-5-[4-(3-methoxy-propyl) -3,4-dihydro-2H-benzo[1,4]oxazin-6-ylmethoxy]-piperidin-2-yl}-2,2, N-trimethyl -propionamide

According to general procedure A, 1.0 mmol of 3-[(2S,4R,5R)-4-[4-((R)-2-ethoxy-propoxymethyl) -phenyl]-5-[4-(3-methoxy-propyl)-3,4-dihydro-2H-benzo[1,4]oxazin-6-ylmethoxy]-1-(toluene-4-sulfonyl)-piperidin-2-yl]-2,2,N-trimethyl-propionamide are reacted to afford the title compound as a pale yellow oil. Rf=0.28 (CH$_2$Cl$_2$/MeOH/ 25% conc. NH$_3$ 200:20:1), Rt=4.08 (gradient I).

The starting materials are prepared as follows:

a) 3-[(2S,4R,5R)-4-[4-((R)-2-Ethoxy-propoxymethyl)-phenyl]-5-[4-(3-methoxy-propyl) -3,4-dihydro-2H-benzo[1,4]oxazin-6-ylmethoxy]-1-(toluene-4-sulfonyl) -piperidin-2-yl]-2,2,N-trimethyl-propionamide According to general procedure D, 1.0 mmol of 3-[(2S,4R,5R)-4-[4((R)-2-ethoxy-propoxymethyl) -phenyl]-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-propionic acid are reacted with methylamine (8M in EtOH) to afford the title compound as a yellow oil. Rf=0.28 (EtOAc/heptane 8:1); Rt=5.29 (gradient I).

b) 3-[(2S,4R,5R)-4-[4-((R)-2-Ethoxy-propoxymethyl)-phenyl]-5-[4-(3-methoxy-propyl) -3,4-dihydro-2H-benzo[1,4]oxazin-6-ylmethoxy]-1-(toluene-4-sulfonyl) -piperidin-2-yl]-2,2-dimethyl-propionic acid To a solution of 1.0 mmol of 3-[(2S,4R,5R)-4-[4-((R)-2-ethoxy-propoxymethyl) -phenyl]-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-propionic acid methyl ester in 10 ml of THF and 10 ml of MeOH are added 10 ml of a 3M lithium hydroxide solution. The reaction mixture is stirred for 4 h at 65° C. The organic solvents are evaporated under reduced pressure and the remaining solution is acidified with 3M aqueous HCl until pH 2. This mixture is extracted with 100 ml of EtOAc (3×). The combined organic layers are washed with brine and dried with Na$_2$SO$_4$. The organic layer is filtered and evaporated under reduced pressure. The residue is purified by flash chromatography (SiO$_2$ 60 F) to afford the title compound as a yellow oil. Rf=0.40 (EtOAc/heptane 3:1); Rt=5.40 (gradient I).

c) 3-[(2S,4R,5R)-4-[4-((R)-2-Ethoxy-propoxymethyl)-phenyl]-5-[4-(3-methoxy-propyl) -3,4-dihydro-2H-benzo[1,4]oxazin-6-ylmethoxy]-1-(toluene-4-sulfonyl) -piperidin-2-yl]-2,2-dimethyl-propionic acid methyl ester To a solution of 4.0 mmol of methyl isobutyrate in 2 ml of THF at −78° C. are added 4.0 mmol of lithiumdiisopropyl amide solution (0.5 M in THF) and the reaction mixture is stirred for 30 min at −78° C. Then 8.0 mmol of hexamethylphosphoramide is added at −78° C. and the mixture is stirred for 30 min. A solution of 1.0 mmol of 6-[(3R,4R,6S) -6-bromomethyl-4-[4-((R)-2-ethoxy-propoxymethyl)-phenyl]-1-(toluene-4-sulfonyl) -piperidin-3-yloxymethyl]-4-(3-methoxy-propyl)-3,4-dihydro-2H-benzo[1,4]oxazine in 2 ml of THF is then added dropwise to the "enolate" at −78° C. and the solution is stirred for 30 min. The reaction mixture is allowed to warm to −12° C. and stirred at this temperature for 40 min. The solution is quenched with 1M aqueous HCl and extracted with 200 ml of EtOAc (3×). The combined organic layers are washed with brine and dried with Na$_2$SO$_4$. The organic layer is filtered and evaporated under reduced pressure. The residue is purified by flash chromatography (SiO$_2$ 60 F) to afford the title compound as yellow oil. Rf=0.41 (EtOAc/heptane 1:3); Rt=5.93 (gradient I).

d) 6-[(3R,4R,6S)-6-Bromomethyl-4-[4-((R)-2-ethoxy-propoxymethyl)-phenyl]-1-(toluene-4-sulfonyl)-piperidin-3-yloxymethyl]-4-(3-methoxy-propyl)-3,4-dihydro-2H-benzo[1,4]oxazine To a solution of 1.0 mmol of methanesulfonic acid (2S,4R,5R)-4-[4-((R)-2-ethoxy-propoxymethyl) -phenyl]-5-[4-(3-methoxy-propyl)-3,4-dihydro-2H-benzo[1,4]oxazin-6-ylmethoxy]-1-(toluene-4-sulfonyl)-piperidin-2-ylmethyl ester (example 1i) in 4 ml of DMF is added 10.0 mmol of lithium bromide and the reaction mixture is stirred for 14 h at 65° C. The reaction mixture is allowed to warm to RT and 100 ml of H$_2$O are added. This mixture is extracted with 100 ml of TBME (3×). The combined organic layers are washed with brine and dried with Na$_2$SO$_4$. The organic layer is filtered and evaporated under reduced pressure. The residue is purified by flash chromatography (SiO$_2$ 60 F) to afford the title compound as a pale yellow resin. Rf=0.41 (EtOAc/heptane 1:1); Rt=6.18 (gradient I).

Example 6

3-{(2R,4R,5R)-4-[4-((R)-2-Ethoxy-propoxymethyl)-phenyl]-5-[4-(3-methoxy-propyl) -3,4-dihydro-2H-benzo[1,4]oxazin-6-ylmethoxy]-piperidin-2-yl}-2,2,N-trimethyl -propionamide The title compound is prepared according to the general procedure A starting from 1.0 mmol of 3-[(2R,4R,5R)-4-[4-((R)-2-ethoxy-propoxymethyl)-phenyl]-5-[4-(3-methoxy-propyl) -3,4-dihydro-2H-benzo[1,4]oxazin-6-ylmethoxy]-1-(toluene-4-sulfonyl) -piperidin-2-yl]-2,2,N-trimethyl-propionamide and is identified based on its Rf value.

The starting materials are prepared as follows:

a) 3-[(2R,4R,5R)-4-[4-((R)-2-Ethoxy-propoxymethyl)-phenyl]-5-[4-(3-methoxy-propyl) -3,4-dihydro-2H-benzo[1,4]oxazin-6-ylmethoxy]-1-(toluene-4-sulfonyl) -piperidin-2-yl]-2,2,N-trimethyl-propionamide According to general procedure D, 1.0 mmol of 3-[(2R,4R,5R)-4-[4-((R)-2-ethoxy-propoxymethyl) -phenyl]-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-propionic acid are reacted with methylamine (8M in EtOH) to afford the title compound which is identified based on its Rf value.

b) 3-[(2R,4R,5R)-4-[4-((R)-2-Ethoxy-propoxymethyl)-phenyl]-5-[4-(3-methoxy-propyl) -3,4-dihydro-2H-benzo[1,4]oxazin-6-ylmethoxy]-1-(toluene-4-sulfonyl) -piperidin-2-yl]-2,2-dimethyl-propionic acid According to the procedure described in example 5b, the title compound is prepared from 1.0 mmol of 3-[(2R,4R,5R)-4-[4((R)-2-ethoxy-propoxymethyl)-phenyl]-5-[4-(3-methoxy-propyl) -3,4-dihydro-2H-benzo[1,4]oxazin-6-ylmethoxy]-1-(toluene-4-sulfonyl) -piperidin-2-yl]-2,2-dimethyl-propionic acid methyl ester and is identified based on its Rf value.

c) 3-[(2R,4R,5R)-4-[4-((R)-2-Ethoxy-propoxymethyl)-phenyl]-5-[4-(3-methoxy-propyl) -3,4-dihydro-2H-benzo[1,4]oxazin-6-ylmethoxy]-1-(toluene-4-sulfonyl) -piperidin-2-yl]-2,2-dimethyl-propionic acid methyl ester To a suspension of 4.0 mmol of potassium tert-butoxide and 0.2 mmol of 18-crown-6 [17455-13-9] in 25 ml of THF at −78° C. are added 1.0 mmol of 3-[(2S,4R,5R)-4-[4-((R)-2-ethoxy-propoxymethyl)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-propionic acid methyl ester in 5 ml of THF and the reaction mixture is stirred for 1 h at −78° C. Then 4.1 mmol of MeI in 3 ml of THF are added at −78° C. and the mixture is stirred for 65 min at −78° C. The reaction mixture is quenched with 0.5 M aqueous HCl to pH 2 and extracted with 200 ml of EtOAc (3×). The combined organic layers are washed with brine and dried with Na$_2$SO$_4$. The organic layer is filtered and evaporated under reduced pressure. The residue is purified by flash chromatography (SiO$_2$ 60 F) to afford the title compound which is identified based on its Rf value.

d) 3-[(2S,4R,5R)-4-[4-((R)-2-Ethoxy-propoxymethyl)-phenyl]-5-[4-(3-methoxy-propyl) -3,4-dihydro-2H-benzo[1,4]oxazin-6-ylmethoxy]-1-(toluene-4-sulfonyl) -piperidin-2-yl]-propionic acid methyl ester To a solution of 1.0 mmol of 3-[(2S,4R,5R)-4-[4-((R)-2-ethoxy-propoxymethyl) -phenyl]-5-[4-(3-methoxy-propyl)-

3,4-dihydro-2H-benzo[1,4]oxazin-6-ylmethoxy]-1-(toluene-4-sulfonyl)-piperidin-2-yl]-propionic acid in 5 ml of MeOH at 0° C. is added 5.0 mmol of TMS-diazomethane (2M in hexane) until the conversion to the methyl ester is complete. The reaction mixture is treated with magnesium sulfate to destroy the excess of TMS-diazomethane. The solids are removed by filtration and the organic layer is concentrated under reduced pressure. The residue is purified by flash chromatography (SiO$_2$ 60 F) to afford the title compound which is identified based on its Rf value.

e) 3-[(2S,4R,5R)-4-[4-((R)-2-Ethoxy-propoxymethyl)-phenyl]-5-[4-(3-methoxy-propyl) -3,4-dihydro-2H-benzo[1,4]oxazin-6-ylmethoxy]-1-(toluene-4-sulfonyl) -piperidin-2-yl]-propionic acid According to the procedure described in example 1g the title compound is prepared from 1.0 mmol of 3-[(2S,4R,5R)-4-[4-((R)-2-ethoxy-propoxymethyl)-phenyl]-5-[4-(3-methoxy-propyl) -3,4-dihydro-2H-benzo[1,4]oxazin-6-ylmethoxy]-1-(toluene-4-sulfonyl) -piperidin-2-yl]-propionitrile and is identified based on its Rf value.

f) 3-[(2S,4R,5R)-4-[4-((R)-2-Ethoxy-propoxymethyl)-phenyl]-5-[4-(3-methoxy-propyl) -3,4-dihydro-2H-benzo[1,4]oxazin-6-ylmethoxy]-1-(toluene-4-sulfonyl) -piperidin-2-yl]-propionitrile According to the procedure described in example 1h the title compound is prepared from 1.0 mmol of methanesulfonic acid 2-[(2R,4R,5R)-4-[4-((R)-2-ethoxy-propoxymethyl) -phenyl]-5-[4-(3-methoxy-propyl)-3,4-dihydro-2H-benzo[1,4]oxazin-6-ylmethoxy]-1-(toluene-4-sulfonyl)-piperidin-2-yl]-ethyl ester and is identified based on its Rf value.

g) Methanesulfonic acid 2-[(2R,4R,5R)-4-[4-((R)-2-ethoxy-propoxymethyl)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-ethyl ester According to the procedure described in example 1i, 1.0 mmol of 2-[(2R,4R,5R)-4-[4-((R)-2-ethoxy-propoxymethyl)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-ethanol are reacted, to afford the title compound as a yellow oil. Rf=0.29 (EtOAc/heptane 2:1); Rt=5.41 (gradient I).

h) 2-[(2R,4R,5R)-4-[4-((R)-2-Ethoxy-propoxymethyl)-phenyl]-5-[4-(3-methoxy-propyl) -3,4-dihydro-2H-benzo[1,4]oxazin-6-ylmethoxy]-1-(toluene-4-sulfonyl) -piperidin-2-yl]-ethanol To a stirred solution of 1.0 mmol of [(2R,4R,5R)-4-[4-((R)-2-ethoxy-propoxymethyl) -phenyl]-5-[4-(3-methoxy-propyl)-3,4-dihydro-2H-benzo[1,4]oxazin-6-ylmethoxy]-1-(toluene-4-sulfonyl)-piperidin-2-yl]-acetic acid (example 1g) in 4 ml of THF are added 2.2 mmol of borane tetrahydrofuran complex (1M in THF) at RT. The reaction mixture is stirred for 3 h, quenched with 60 ml of MeOH and concentrated under reduced pressure. The residue is purified by flash chromatography (SiO$_2$ 60 F) to afford the title compound as a yellow oil. Rf=0.35 (EtOAc); Rt=5.15 (gradient I).

Example 7

N-(2-{(2R,4R,5R)-4-[4-((R)-2-Ethoxy-propoxymethyl)-phenyl]-5-[4-(3-methoxy-propyl) -3,4-dihydro-2H-benzo[1,4]oxazin-6-ylmethoxy]-piperdin-2-yl}-1,1-dimethyl-ethyl) -acetamide The title compound is prepared according to the general procedure A starting from 1.0 mmol of N-{2-[(2R,4R,5R)-4-[4-((R)-2-ethoxy-propoxymethyl)-phenyl]-5-[4-(3-methoxy-propyl) -3,4-dihydro-2H-benzo[1,4]oxazin-6-ylmethoxy]-1-(toluene-4-sulfonyl) -piperidin-2-yl]-1,1-dimethyl-ethyl}-acetamide and is identified based on its Rf value.

The starting materials are prepared as follows:

a) N-{2-[(2R,4R,5R)-4-[4-((R)-2-Ethoxy-propoxymethyl)-phenyl]-5-[4-(3-methoxy-propyl) -3,4-dihydro-2H-benzo[1,4]oxazin-6-ylmethoxy]-1-(toluene-4-sulfonyl) -piperidin-2-yl]-1,1-dimethyl-ethyl}-acetamide To a solution of 1.0 mmol of 2-[(2R,4R,5R)-4-[4-((R)-2-ethoxy-propoxymethyl) -phenyl]-5-[4-(3-methoxy-propyl)-3,4-dihydro-2H-benzo[1,4]oxazin-6-ylmethoxy]-1-(toluene-4-sulfonyl)-piperidin-2-yl]-1,1-dimethyl-ethylamine, 3.0 mmol of Et$_3$N in 10 ml of CH$_2$Cl$_2$ are added 1.5 mmol of acetyl chloride at 0° C. and the resulting mixture is stirred for 1 h. The reaction mixture is diluted with water and extracted with CH$_2$Cl$_2$. The organic phases are combined, dried over Na$_2$SO$_4$ and concentrated under reduced pressure. The residue is purified by flash chromatography (SiO$_2$ 60 F) to afford the title compound which is identified based on its Rf value.

b) 2-[(2R,4R,5R)-4-[4-((R)-2-Ethoxy-propoxymethyl)-phenyl]-5-[4-(3-methoxy-propyl) -3,4-dihydro-2H-benzo[1,4]oxazin-6-ylmethoxy]-1-(toluene-4-sulfonyl) -piperidin-2-yl]-1,1-dimethyl-ethylamine The title compound is prepared according to the general procedure E starting from 1.0 mmol of {2-[(2R,4R,5R)-4-[4-((R)-2-ethoxy-propoxymethyl)-phenyl]-5-[4-(3-methoxy-propyl) -3,4-dihydro-2H-benzo[1,4]oxazin-6-ylmethoxy]-1-(toluene-4-sulfonyl) -piperidin-2-yl]-1,1-dimethyl-ethyl}-carbamic acid benzyl ester and is identified based on its Rf value.

c) {2-[(2R,4R,5R)-4-[4-((R)-2-Ethoxy-propoxymethyl)-phenyl]-5-[4-(3-methoxy-propyl) -3,4-dihydro-2H-benzo[1,4]oxazin-6-ylmethoxy]-1-(toluene-4-sulfonyl) -piperidin-2-yl]-1,1-dimethyl-ethyl}-carbamic acid benzyl ester A mixture of 1.0 mmol of 6-[(3R,4R,6R)-6-(2-isocyanato-2-methyl-propyl)-4-[4-((R)-2-ethoxy-propoxymethyl)-phenyl]-1-(toluene-4-sulfonyl)-piperidin-3-yloxymethyl]-4-(3-methoxy-propyl) -3,4-dihydro-2H-benzo[1,4]oxazine and 20.0 mmol of benzyl alcohol is heated at 115° C. for 14 h. The reaction mixture is directly purified by flash chromatography (SiO$_2$ 60 F) to afford the title compound which is identified based on its Rf value.

d) 6-[(3R,4R,6R)-6-(2-Isocyanato-2-methyl-propyl)-4-[4-((R)-2-ethoxy-propoxymethyl) -phenyl]-1-(toluene-4-sulfonyl)-piperidin-3-yloxymethyl]-4-(3-methoxy-propyl) -3,4-dihydro-2H-benzo[1,4]oxazine A solution of 1.0 mmol of 3-[(2R,4R,5R)-4-[4-((R)-2-ethoxy-propoxymethyl)-phenyl]-5-[4-(3-methoxy-propyl)-3,4-dihydro-2H-benzo[1,4]oxazin-6-ylmethoxy]-1-(toluene-4-sulfonyl) -piperidin-2-yl]-2,2-dimethyl-propionyl azide in 10 ml of toluene is heated at 115° C. for 1.5 h. The reaction mixture is concentrated under reduced pressure to afford the crude title compound which is identified based on its Rf value.

e) 3-[(2R,4R,5R)-4-[4-((R)-2-Ethoxy-propoxymethyl)-phenyl]-5-[4-(3-methoxy-propyl) -3,4-dihydro-2H-benzo[1,4]oxazin-6-ylmethoxy]-1-(toluene-4-sulfonyl) -piperidin-2-yl]-2,2-dimethyl-propionyl azide To a solution of 1.0 mmol of 3-[(2R,4R,5R)-4-[4-((R)-2-ethoxy-propoxymethyl) -phenyl]-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-propionic acid (example 6b) and 2.5 mmol of Et$_3$N in 10 ml of THF is added 2.0 mmol of ethyl chloroformate at 0° C. and the mixture is stirred for 1 h at 0° C. Then a solution of 20.0 mmol of sodium azide in 5 ml of water is added dropwise and the reaction mixture is stirred at 0° C. for 45 min. The mixture is diluted with 2 ml of water. This mixture is extracted with 50 ml of EtOAc (3×) and the combined organic layers are washed with water (2×) and dried with $Na_2SO_4$. The organic layer is filtered and evaporated under reduced pressure to afford the corresponding crude acyl azide which is identified based on its Rf value.

Example 8

6-[(3R,4R,6R)-4-[4-((R)-2-Ethoxy-propoxymethyl)-phenyl]-6-(4-methyl-4H-[1,2,4]triazol-3-ylmethyl)-piperidin-3-yloxymethyl]-4-(3-methoxy-propyl)-3,4-dihydro-2H-benzo[1,4]oxazine According to general procedure A, 1.0 mmol of 6-[(3R,4R,6R)-4-[4-((R)-2-ethoxy-propoxymethyl) -phenyl]-6-(4-methyl-4H-[1,2,4]triazol-3-ylmethyl)-1-(toluene-4-sulfonyl) -piperidin-3-yloxymethyl]-4-(3-methoxy-propyl)-3,4-dihydro-2H-benzo[1,4]oxazine is used to afford the title compound, which is identified based on its Rf value.

The starting materials are prepared as follows:
a) 6-[(3R,4R,6R)-4-[4-((R)-2-Ethoxy-propoxymethyl)-phenyl]-6-(4-methyl-4H-[1,2,4]triazol-3-ylmethyl)-1-(toluene-4-sulfonyl)-piperidin-3-yloxymethyl]-4-(3-methoxy-propyl) -3,4-dihydro-2H-benzo[1,4]oxazine Into a solution of 1.0 mmol of [(2R,4R,5R)-4-[4-((R)-2-ethoxy-propoxymethyl)-phenyl]-5-[4-(3-methoxy-propyl)-3,4-dihydro-2H-benzo[1,4]oxazin-6-ylmethoxy]-1-(toluene-4-sulfonyl) -piperidin-2-yl]-acetic acid [1-dimethylamino-meth-(E)-ylidene]- hydrazide in 2 ml of acetonitrile is condensed ca. 1 ml of gaseous methylamine, at RT. Acetic acid (2 mL) is carefully added, then the reaction system is sealed, and heated at 100° C. for 4 h. The reaction mixture is cooled to RT, poured into saturated aqueous $NaHCO_3$, and extracted with EtOAc (3×). The combined organic extracts are dried over $Na_2SO_4$, concentrated under reduced pressure, and purified by flash chromatography ($SiO_2$ 60 F), to afford the title compound, which is identified based on its Rf value.

b) [(2R,4R,5R)-4-[4-((R)-2-Ethoxy-propoxymethyl)-phenyl]-5-[4-(3-methoxy-propyl) -3,4-dihydro-2H-benzo[1,4]oxazin-6-ylmethoxy]-1-(toluene-4-sulfonyl)-piperidin-2-yl]-acetic acid [1-dimethylamino-meth-(E)-ylidene]-hydrazide A solution of 1.0 mmol of [(2R,4R,5R)-4-[4-((R)-2-ethoxy-propoxymethyl)-phenyl]-5-[4-(3-methoxy-propyl)-3,4-dihydro-2H-benzo[1,4]oxazin-6-ylmethoxy]-1-(toluene-4-sulfonyl) -piperidin-2-yl]-acetic acid hydrazide in 5 ml of $CH_2Cl_2$ is treated at RT with 1.1 mmol of N,N-dimethyl-formamide dimethylacetal and refluxed for 1 h. The mixture is cooled to RT, and concentrated under reduced pressure to afford the title compound, which is identified based on its Rf value.

c) [(2R,4R,5R)-4-[-((R)-2-Ethoxy-propoxymethyl)-phenyl]-5-[4-(3-methoxy-propyl) -3,4-dihydro-2H-benzo[1,4]oxazin-6-ylmethoxy]-1-(toluene-4-sulfonyl)-piperidin-2-yl]-acetic acid hydrazide A solution of 1.0 mmol of N'-{2-[(2R,4R,5R)-4-[4-((R)-2-ethoxy-propoxymethyl) -phenyl]-5-[4-(3-methoxy-propyl)-3,4-dihydro-2H-benzo[1,4]oxazin-6-ylmethoxy]-1-(toluene-4-sulfonyl)-piperidin-2-yl]-acetyl}-hydrazinecarboxylic acid tert-butyl ester in 13 ml of $CH_2Cl_2$ is treated at 0° C. with 3.3 ml of trifluoroacetic acid. The reaction mixture is stirred at 0° C. for 1 h, then at RT for 3 h and diluted with $CH_2Cl_2$, basified with saturated aqueous $NaHCO_3$. The aqueous layer is extracted 2× with $CH_2Cl_2$, the combined organic extracts are washed with $H_2O$, then with brine, dried over $Na_2SO_4$, and concentrated under reduced pressure, affording the title compound, which is identified based on its Rf value.

d) N'-{2-[(2R,4R,5R)-4-[4-((R)-2-Ethoxy-propoxymethyl)-phenyl]-5-[4-(3-methoxy-propyl) -3,4-dihydro-2H-benzo[1,4]oxazin-6-ylmethoxy]-1-(toluene-4-sulfonyl) -piperidin-2-yl]-acetyl}-hydrazinecarboxylic acid tert-butyl ester A solution of 1.0 mmol of [(2R,4R,5R)-4-[4-((R)-2-ethoxy-propoxymethyl)-phenyl]-5-[4-(3-methoxy-propyl)-3,4-dihydro-2H-benzo[1,4]oxazin-6-ylmethoxy]-1-(toluene-4-sulfonyl) -piperidin-2-yl]-acetic acid (example 1g) in 5 ml of $CH_2Cl_2$ is treated at RT with 1.5 mmol of 1-chloro-N,N,2-trimethylpropenylamine, and stirred at RT for 2.5 h. This solution is added slowly, at 0° C., to a solution of 5 mmol of tert-butyl carbazate [870-46-2] and 5 mmol of $Et_3N$ in 1 ml of $CH_2Cl_2$. The reaction mixture is stirred at 4° C. for 16.5 h, then quenched with $H_2O$. The aqueous layer is extracted with $CH_2Cl_2$ (2×). The combined organic extracts are washed with brine, dried over $Na_2SO_4$, and concentrated under reduced pressure. The residue is purified by flash chromatography ($SiO_2$ 60 F) to afford the title compound, which is identified based on its Rf value.

Example 9

6-[(3R,4R,6R)-4-[4-((R)-2-Ethoxy-propoxymethyl)-phenyl]-6-(2-[1,2,4]triazol-4-yl-ethyl) -piperidin-3-yloxymethyl]-4-(3-methoxy-propyl)-3,4-dihydro-2H-benzo[1,4]oxazine According to general procedure A, 1.0 mmol of 6-[(3R,4R,6R)-4-[4-((R)-2-ethoxy-propoxymethyl) -phenyl]-1-(toluene-4-sulfonyl)- 6-(2-[1,2,4]triazol-4-yl-ethyl)-piperidin-3-yloxymethyl]-4-(3-methoxy-propyl)-3,4-dihydro-2H-benzo[1,4]oxazine are used to afford the title compound as a yellow oil. Rf=0.13 ($CH_2Cl_2$/MeOH/25% conc. $NH_3$ 200:20:1); Rt=3.67 (gradient I).

The starting materials are prepared as follows:
a) 6-[(3R,4R,6R)-4-[4-((R)-2-Ethoxy-propoxymethyl)-phenyl]-1-(toluene-4-sulfonyl) -6-(2-[1,2,4]triazol-4-yl-ethyl)-piperidin-3-yloxymethyl]-4-(3-methoxy-propyl)-3,4-dihydro-2H-benzo[1,4]oxazine To a solution of 1.0 mmol of 2-[(2R,4R,5R)-4-[4-((R)-2-ethoxy-propoxymethyl) -phenyl]-5-[4-(3-methoxy-propyl)-3,4-dihydro-2H-benzo[1,4]oxazin-6-ylmethoxy]-1-(toluene-4-sulfonyl)-piperidin-2-yl]-ethylamine and 3.5 mmol of N,N-dimethyl-formamidazine [16114-05-9] in 5 ml of toluene is treated at RT with 0.1 mmol of p-toluenesulfonic acid. The reaction mixture is stirred at 80° C. for 20 h, cooled to RT, and diluted with EtOAc. The organic phase is washed sequentially with 1N citric acid, saturated aqueous $NaHCO_3$ and brine, dried over $Na_2SO_4$, and concentrated under reduced pressure. The residue is purified by flash chromatography ($SiO_2$, 60 F), to afford the title compound as a yellow oil. Rf=0.27 ($CH_2Cl_2$/MeOH/25% conc. $NH_3$ 200:20:1); Rt=4.83 (gradient).

b) 2-[(2R,4R,5R)-4-[4-((R)-2-Ethoxy-propoxymethyl)-phenyl]-5-[4-(3-methoxy-propyl) -3,4-dihydro-2H-benzo[1,4]oxazin-6-ylmethoxy]-1-(toluene-4-sulfonyl) -piperidin-2-yl]-ethylamine According to general procedure E, 1.0 mmol of 6-[(3R,4R,6R)-6-(2-azido-ethyl)-4-[4-((R)-2-ethoxy-propoxymethyl)-phenyl]-1-(toluene-4-sulfonyl)-piperidin-3-yloxymethyl]-4-(3-methoxy-propyl)-3,4-dihydro-2H-benzo[1,4]oxazine is reacted in MeOH, to afford the title compound as a pale yellow oil. Rf=0.44 (CH$_2$Cl$_2$/MeOH/25% conc. NH$_3$ 200:20:1); Rt=4.78 (gradient I).

c) 6-[(3R,4R,6R)-6-(2-Azido-ethyl)-4-[4-((R)-2-ethoxy-propoxymethyl)-phenyl]-1-(toluene-4-sulfonyl)-piperidin-3-yloxymethyl]-4-(3-methoxy-propyl)-3,4-dihydro-2H-benzo[1,4]oxazine A solution of 1.0 mmol of methanesulfonic acid 2-[(2R,4R,5R)-4-[4-((R)-2-ethoxy-propoxymethyl) -phenyl]-5-[4-(3-methoxy-propyl)-3,4-dihydro-2H-benzo[1,4]oxazin-6-ylmethoxy]-1-(toluene-4-sulfonyl)-piperidin-2-yl]-ethyl ester (example 6g) and 10 mmol of sodium azide in 1.5 ml of DMPU is stirred at 80° C. for 3 h. The solution is cooled to RT, diluted with 3 ml of TBME, filtered through 2 cm of SiO$_2$ 60 F, eluting with EtOAc-Heptane 1:1. The filtrate is concentrated under reduced pressure and purified by flash chromatography (SiO2 60 F), to afford the title compound as a yellow oil. Rf=0.45 (EtOAc/heptane 2:1); Rt=5.80 (gradient I).

Example 10

6-{(3R,4R,6R)-4-[4(R)-2-Ethoxy-propoxymethyl)-phenyl]-6-morpholin-4-ylmethyl -piperidin-3-yloxymethyl}-4-(3-methoxy-propyl)-3,4-dihydro-2H-benzo[1,4]oxazine According to general procedure A, 1.0 mmol of 6-[(3R,4R,6R)-4-[4-((R)-2-ethoxy-propoxymethyl) -phenyl]-6-morpholin-4-ylmethyl-1-(toluene-4-sulfonyl)-piperidin-3-yloxymethyl]-4-(3-methoxy- propyl)-3,4-dihydro-2H-benzo[1,4]oxazine are reacted to afford the title compound, which is identified based on its Rf value.

The starting materials are prepared as follows:

a) 6-[(3R,4R,6R)-4-[4-((R)-2-Ethoxy-propoxymethyl)-phenyl]-6-morpholin-4-ylmethyl-1-(toluene-4-sulfonyl)-piperidin-3-yloxymethyl]-4-(3-methoxy-propyl)-3,4-dihydro-2H-benzo[1,4]oxazine A solution of 1.0 mmol of C-[(2R,4R,5R)-4-[4-((R)-2-ethoxy-propoxymethyl)-phenyl]-5-[4-(3-methoxy-propyl)-3,4- dihydro-2H-benzo[1,4]oxazin-6-ylmethoxy]-1-(toluene-4-sulfonyl) -piperidin-2-yl]-methylamine in 7 ml of DMSO at RT is treated with 4 mmol of Et$_3$N, followed by 1.2 mmol of (bis-2-bromoethyl)ether [4497-29-4]. The reaction mixture is stirred at 40° C. for 16 h, cooled to RT, and diluted with EtOAc. The organic phase is washed 2× with H$_2$O. The combined aqueous phases are extracted with EtOAc. The combined organic extracts are dried over Na$_2$SO$_4$ and concentrated under reduced pressure. The residue is purified by flash chromatography (SiO$_2$, 60 F), to afford the title compound, which is identified based on its Rf value.

b) C-[(2R,4R,5R)-4-[4(R)-2-Ethoxy-propoxymethyl)-phenyl]-5-[4-(3-methoxy-propyl) -3,4-dihydro-2H-benzo[1,4]oxazin-6-ylmethoxy]-1-(toluene-4-sulfonyl) -piperidin-2-yl]-methylamine According to general procedure E, 1.0 mmol of [(2R,4R,5R)-4-[4-((R)-2-ethoxy-propoxy-methyl) -phenyl]-5-[4-(3-methoxy-propyl)-3,4-dihydro-2H-benzo[1,4]oxazin-6-ylmethoxy]-1-(toluene-4-sulfonyl)-piperidin-2-ylmethyl]-carbamic acid benzyl ester is reacted in MeOH, to afford the title compound, which is identified based on its Rf value.

c) [(2R,4R,5R)-4-[4(R)-2-Ethoxy-propoxymethyl)-phenyl]-5-[4-(3-methoxy-propyl) -3,4-dihydro-2H-benzo[1,4]oxazin-6-ylmethoxy]-1-(toluene-4-sulfonyl)-piperidin-2-ylmethyl]acid benzyl ester A solution of 1.0 mmol of 6-[(3R,4R,6R)-6-isocyanatomethyl-4-[4-((R)-2-ethoxy-propoxymethyl) -phenyl]-1-(toluene-4-sulfonyl)-piperidin-3-yloxymethyl]-4-(3-methoxy-propyl) -3,4-dihydro-2H-benzo[1,4]oxazine and 1 ml of benzyl alcohol is stirred at 120° C. for 3 h. The reaction mixture is cooled at RT, and purified by flash chromatography (SiO$_2$ 60 F) to afford the title compound, which is identified based on its Rf value.

d) 6-[(3R,4R,6R)-6-Isocyanatomethyl-4-[4-((R)-2-ethoxy-propoxymethyl)-phenyl]-1-(toluene-4-sulfonyl)-piperidin-3-yloxymethyl]-4-(3-methoxy-propyl)-3,4-dihydro-2H-benzo[1,4]oxazine To a solution of 1.0 mmol of [(2R,4R,5R)-4-[4(R)-2-ethoxy-propoxymethyl)-phenyl]-5-[4-(3-methoxy-propyl)-3,4- dihydro-2H-benzo[1,4]oxazin-6-ylmethoxy]-1-(toluene-4-sulfonyl) -piperidin-2-yl]-acetic acid (example 1g) and 2.5 mmol of Et$_3$N in 10 ml of THF are added 2 mmol of ethyl chloroformate at 0° C. and the mixture is stirred for 1 h at 0° C. Then a solution of 20 mmol of sodium azide in 2 ml of water is added drop-wise and the reaction mixture is stirred at 0° C. for 1 h. The mixture is diluted with 40 ml of EtOAc and washed with 3×5 ml of H$_2$O. The organic layer is dried over Na$_2$SO$_4$, and evaporated under reduced pressure. The residue is redissolved in 5 ml of toluene and heated to 120° C. for 1.5 h. The toluene is evaporated under reduced pressure yielding the crude title compound, which is identified based on its Rf value.

The invention claimed is:

1. A compound of the formula

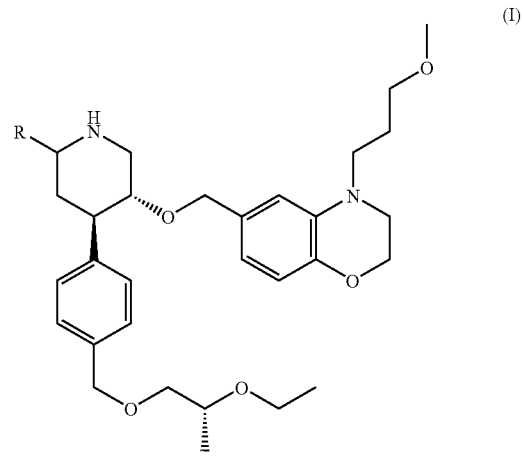

or its pharmaceutically acceptable salt, in which

R is
C$_{2-8}$-alkenyl,
C$_{2-8}$-alkynyl,
C$_{0-8}$-alkyl-carbonyl-optionally N-mono-C$_{1-8}$-alkylated amino-C$_{1-8}$-alkyl,
C$_{3-8}$-cycloalkyl-C$_{0-8}$-alkyl,
C$_{1-8}$-alkyl-sulfonyl-C$_{1-8}$-alkyl,
optionally N-mono- or N,N-di-C$_{1-8}$-alkylated carbamoyl-C$_{0-8}$-alkyl,
optionally O—C$_{1-8}$-alkylated carboxyl-C$_{0-8}$-alkyl,
optionally N and/or N' mono-, di- or tri-C$_{1-8}$-alkylated ureido-C$_{1-8}$-alkyl,
heterocyclylcarbonyl-C$_{0-8}$-alkyl or
heterocyclyl-C$_{0-8}$-alkyl;
each of said radicals may be substituted by 1-4 substituents independently selected from
C$_{1-8}$-alkoxy,
C$_{1-8}$-alkoxy-C$_{1-8}$-alkoxy,
C$_{1-8}$-alkyl, cyano,
halogen,
hydroxyl,
oxo,
trifluoromethoxy and
trifluoromethyl.

2. The compound according to claim 1, which corresponds to formulae (IA) or (IB)

(IA)

(IB)

or a or a pharmaceutically acceptable salt thereof, where the meaning of the substituent R is as indicated for compounds of the formula (I) according to claim 1.

3. The compound according to claim 1 or 2 in which
R is $C_{0-8}$-alkyl-carbonyl-optionally N-mono-$C_{1-8}$-alkylated amino-$C_{1-8}$-alkyl,
optionally substituted by 1-2 substituents independently selected from
$C_{1-8}$-alkoxy,
$C_{1-8}$-alkoxy-$C_{1-8}$-alkoxy,
$C_{1-8}$-alkyl,
cyano,
halogen,
hydroxyl,
oxo,
trifluoromethoxy and
trifluoromethyl or a pharmaceutically acceptable salt thereof.

4. The compound according to claim 1 or 2 in which
R is optionally N-mono- or N,N-di-$C_{1-8}$-alkylated carbamoyl-$C_{0-8}$-alkyl,
optionally substituted by 1-2 substituents independently selected from
$C_{1-8}$-alkoxy,
$C_{1-8}$-alkoxy-$C_{1-8}$-alkoxy,
$C_{1-8}$-alkyl,
cyano,
halogen,
hydroxyl,
oxo,
trifluoromethoxy and
trifluoromethyl or a pharmaceutically acceptable salt thereof.

5. The compound according to claim 1 or 2 in which
R is optionally N and/or N' mono-, di- or tri-$C_{1-8}$-alkylated ureido-$C_{1-8}$-alkyl,
optionally substituted by 1-2 substituents independently selected from
$C_{1-8}$-alkoxy,
$C_{1-8}$-alkoxy-$C_{1-8}$-alkoxy,
$C_{1-8}$-alkyl,
cyano,
halogen,
hydroxyl,
oxo,
trifluoromethoxy and
trifluoromethyl or a pharmaceutically acceptable salt thereof.

6. The compound according to claim 1 or 2 in which
R is heterocyclyl-$C_{0-8}$-alkyl,
optionally substituted by 1-2 substituents independently selected from
$C_{1-8}$-alkoxy,
$C_{1-8}$-alkoxy-$C_{1-8}$-alkoxy,
$C_{1-8}$-alkyl,
cyano,
halogen,
hydroxyl,
oxo,
trifluoromethoxy and
trifluoromethyl or a pharmaceutically acceptable salt thereof.

7. The compound according to claim 1 or 2 in which
R is $C_{0-8}$-alkyl-carbonyl-optionally N-mono-$C_{1-8}$-alkylated amino-$C_{1-8}$-alkyl,
optionally N-mono- or N,N-di-$C_{1-8}$-alkylated carbamoyl-$C_{0-8}$-alkyl or
heterocyclyl-$C_{0-8}$-alkyl or a pharmaceutically acceptable salt thereof.

8. The compound according to claim 1 or 2 in which
R is $C_{0-4}$-alkyl-carbonyl-optionally N-mono-$C_{1-4}$-alkylated amino-$C_{1-4}$-alkyl,
optionally N-mono- or N,N-di-$C_{1-8}$-alkylated carbamoyl-$C_{0-4}$-alkyl, morpholinyl-$C_{0-4}$-alkyl,
tetrazolyl-$C_{0-4}$-alkyl or triazolyl-$C_{0-4}$-alkyl or a pharmaceutically acceptable salt thereof.

9. A pharmaceutical composition comprising a compound according to claim 1; or a pharmaceutically acceptable salt thereof; and a pharmaceutically inert inorganic or organic excipient.

10. A method for the treatment, or for the delay of progression of hypertension, heart failure, renal failure, or stroke or comprising administering a therapeutically effective amount of a compound according to claim 1 or a pharmaceutically acceptable salt thereof to a subject in need thereof.

11. A pharmaceutical composition comprising a compound according to claim 1 or a pharmaceutically acceptable salt thereof, and one or more agents having cardiovascular activity.

12. The compound according to claim 7 in which
R is $C_{0-4}$-alkyl-carbonyl-optionally N-mono-$C_{1-4}$-alkylated amino-$C_{1-4}$-alkyl, optionally N-mono- or N,N-di-$C_{1-8}$-alkylated carbamoyl-$C_{0-4}$-alkyl, morpholinyl-$C_{0-4}$-alkyl, tetrazolyl-$C_{0-4}$-alkyl or triazolyl-$C_{0-4}$-alkyl or a pharmaceutically acceptable salt thereof.

* * * * *